United States Patent [19]

Reasons et al.

[11] 4,328,185
[45] May 4, 1982

[54] AUTOMATED CHEMICAL TESTING APPARATUS

[75] Inventors: Robert Reasons, Santa Ana; Bill E. Albright, Laguna Niguel, both of Calif.

[73] Assignee: Boehringer Mannheim Corporation, Indianapolis, Ind.

[21] Appl. No.: 163,093

[22] Filed: Jun. 26, 1980

[51] Int. Cl.³ .............................................. G01N 35/08
[52] U.S. Cl. ........................................ 422/82; 422/81
[58] Field of Search ................ 422/81, 82; 23/230 R

[56] References Cited

U.S. PATENT DOCUMENTS 3,690,833  9/1972  Ferrari .............................. 422/82 X

*Primary Examiner*—Ronald Serwin
*Attorney, Agent, or Firm*—Woodard, Weikart, Emhardt & Naughton

[57] ABSTRACT

An automated chemical testing apparatus which includes a continuous flow front end portion and a discrete flow back end portion. Also provided is a collecting means for separately collecting these sample segments and the intersample segments, means for analyzing these sample segments, and a waste collection means for collecting waste fluids.

17 Claims, 53 Drawing Figures

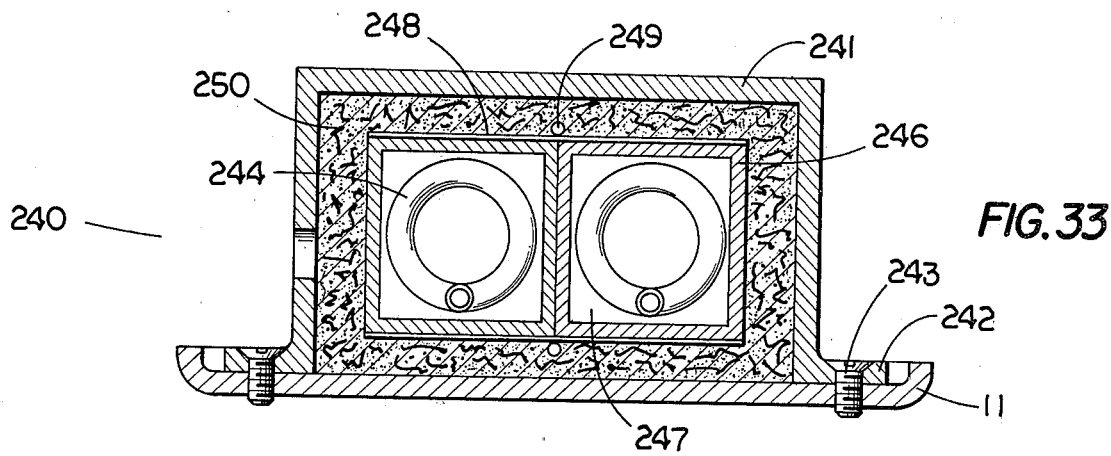
FIG. 33
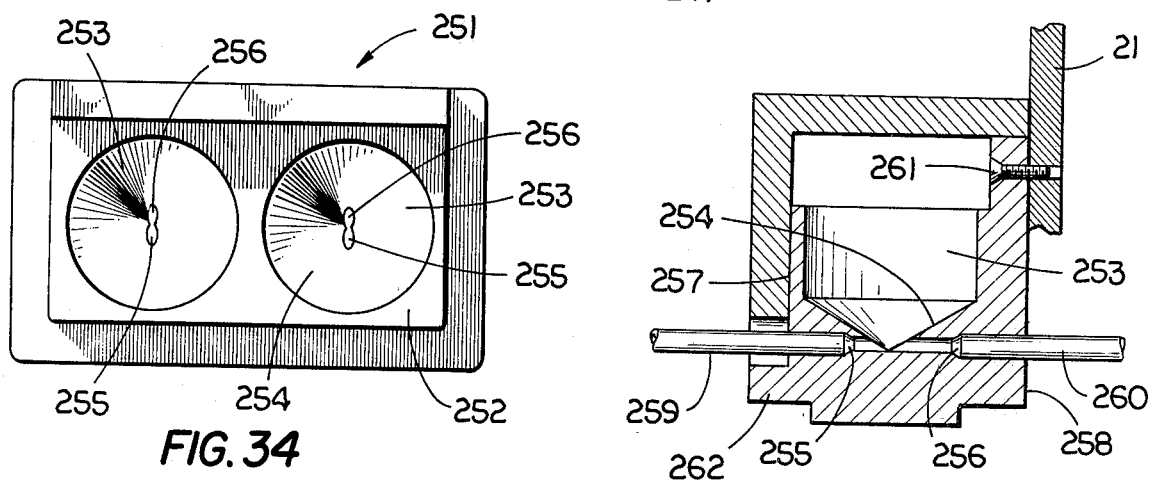
FIG. 34
FIG. 36
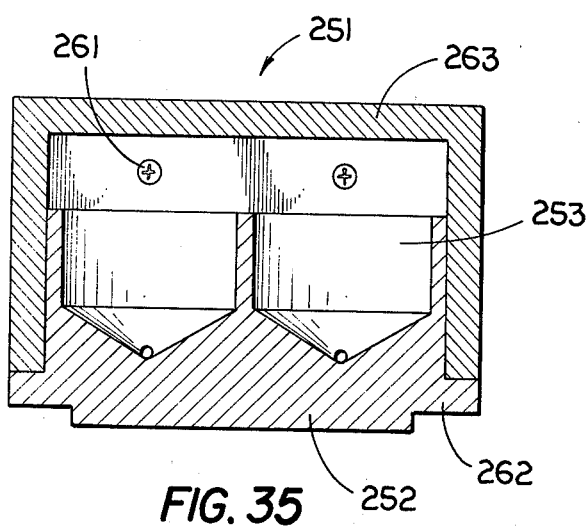
FIG. 35
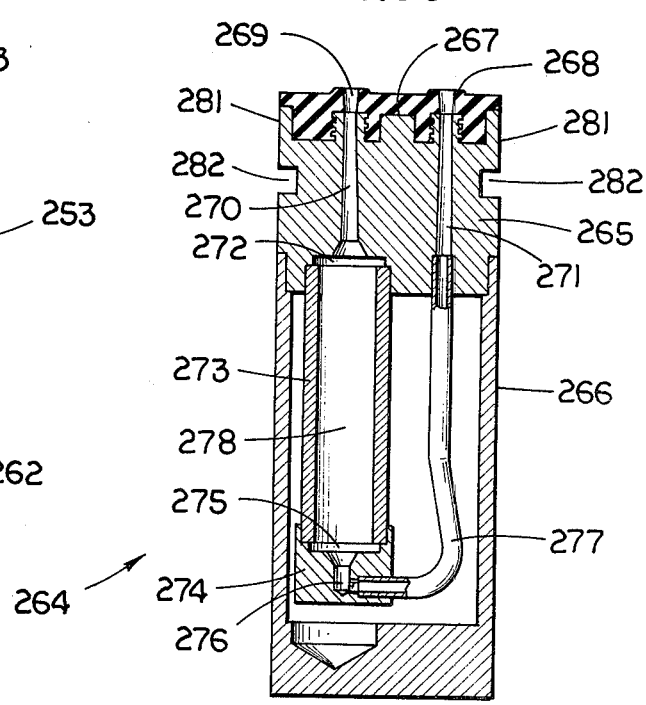
FIG. 37

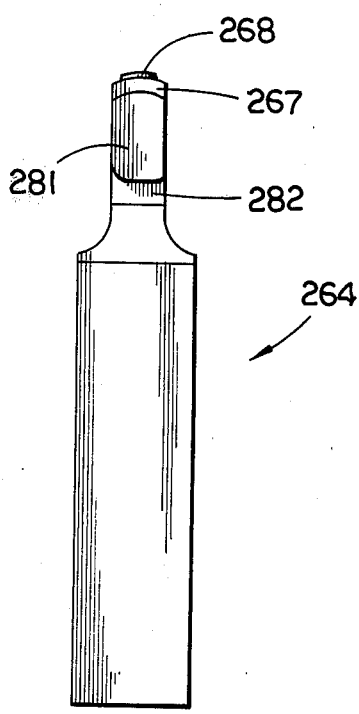
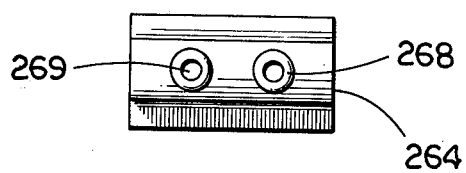
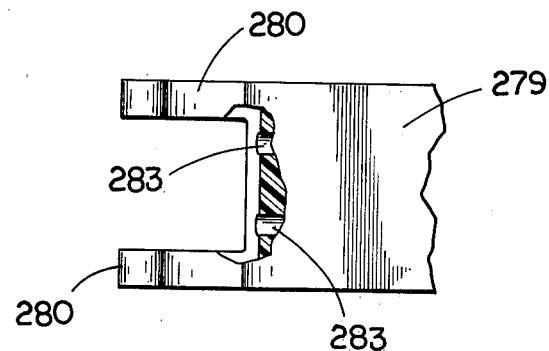
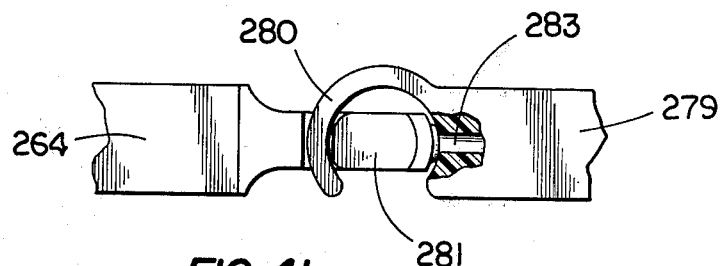
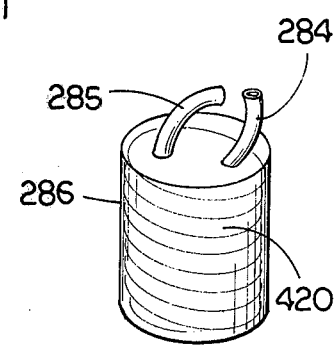
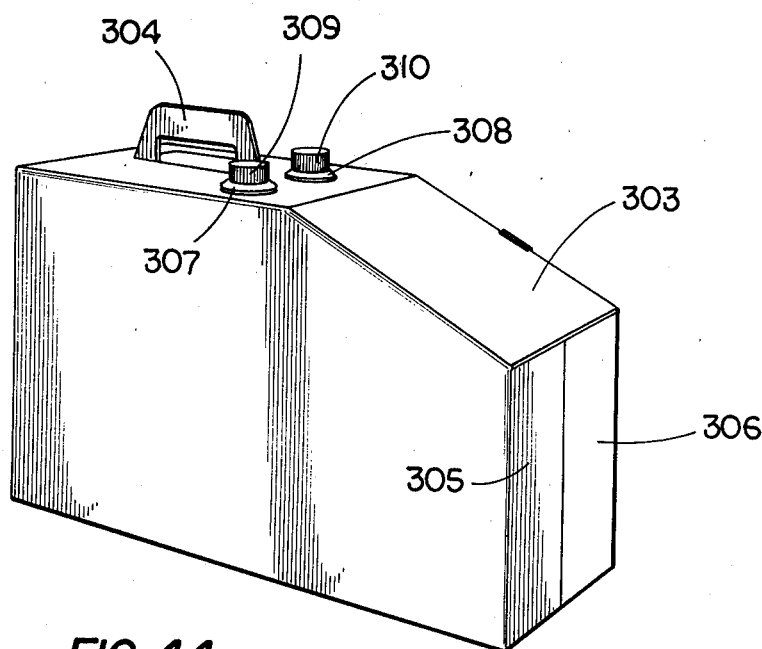

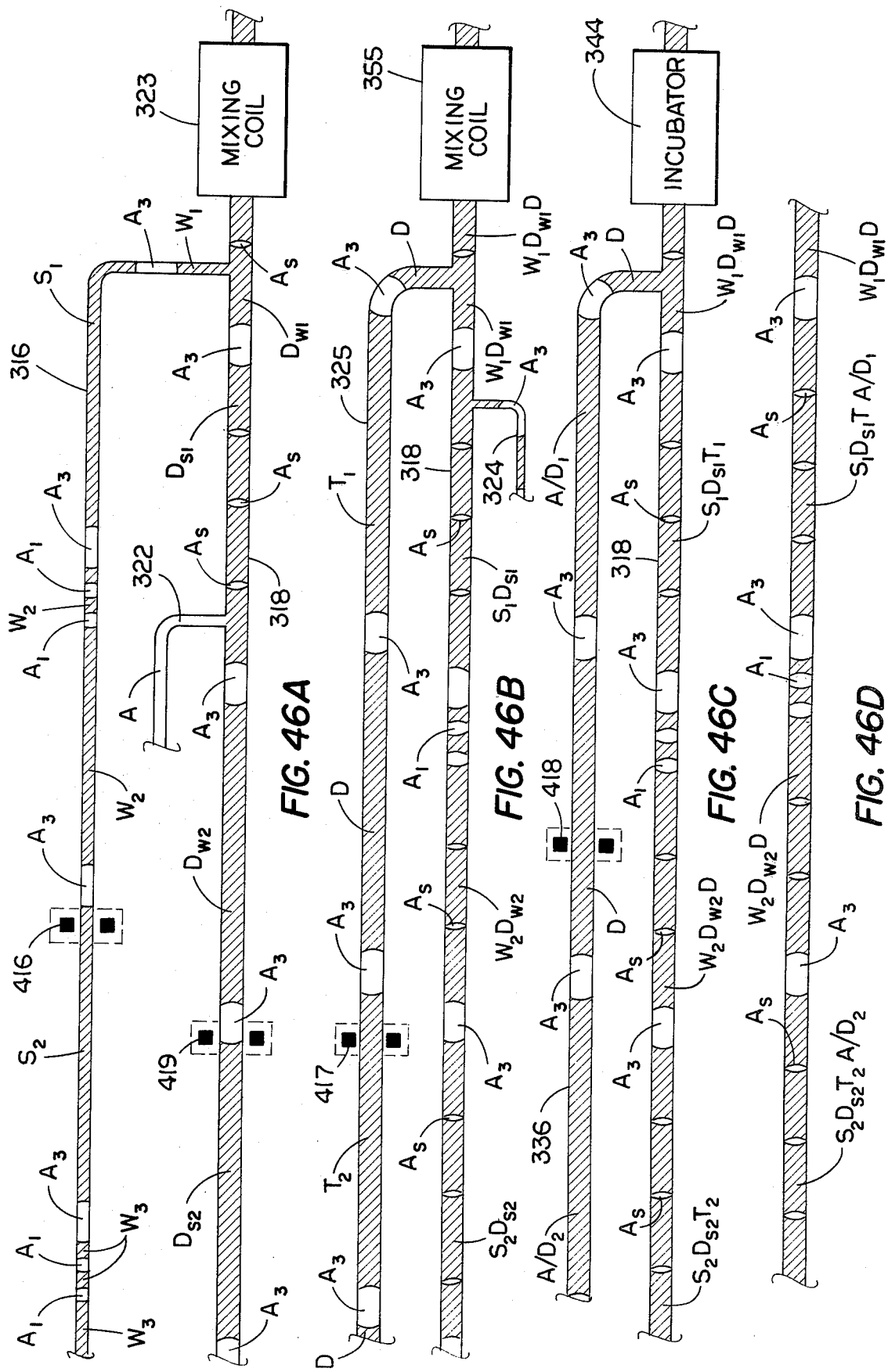

AUTOMATED CHEMICAL TESTING APPARATUS

BACKGROUND OF THE INVENTION

1. Field of the Invention

The present invention relates to an automated chemical testing apparatus, and more particularly to an apparatus utilizing combined continuous and discrete flow portions to conduct an assay of a sample.

2. Description of the Prior Art

The present invention provides an automated chemical testing apparatus which utilizes the combination of both continuous and discrete flow of the sample and reagents to perform the assay procedure. In the prior art, there is disclosed a number of automated testing apparatus which utilize continuous flow throughout the system. As will be shown and described herein, the combination of continuous and discrete flow portions is advantageous in several respects. Examples of the continuous flow testing devices of the prior art are those marketed by the Technicon Instruments Corporation, Tarrytown, New York; Nova Biomedical, 1238 Chestnut Street, Newton, Mass.; and the Squibb company.

SUMMARY OF THE INVENTION

One aspect of the present invention is an automated chemical testing apparatus comprising a means for providing a continuous flow stream of alternating sample and intersample fluid segments, means for separately collecting each of the sample and intersample segments, means for analyzing the sample segments, means for collecting waste fluids, and means for alternately flowing the collected sample segments to the analysis means and the intersample segments to the waste collection means. In a related aspect, the present apparatus provides for the maintenance of the sample segments in the stationary condition during analysis. The present invention also provides a testing apparatus including means for drawing sample and intersample segments into the apparatus, for moving the segments through the flow path of the apparatus, for introducing reagent and diluent to the sample segments and for separating the test components of a sample segment from the waste components for analysis.

It is an object of the present invention to provide a chemical testing apparatus which includes continuous and discrete flow portions.

A further object of the present invention is to provide a testing apparatus which is reliable and accurate in operation.

It is another object of the present invention to provide a chemical testing apparatus which is readily adaptable to a variety of assay procedures.

Further objects and advantages of the present invention will become apparent from the description of the preferred embodiment which follows.

BRIEF DESCRIPTION OF THE DRAWINGS

FIG. 33 is an elevational cross-sectional view of the incubator assembly of FIG. 32.

FIG. 34 is a top, plan view of a collection cup unit useful in the present invention.

FIG. 35 is a front, cross-sectional view of the wash cups of FIG. 34.

FIG. 36 is an end, cross-sectional view of the wash cups of FIG. 34.

FIG. 37 is a front, cross-sectional view of a cassette useful in the present invention.

FIG. 38 is a side, elevational view of the cassette of FIG. 37.

FIG. 39 is a top, plan view of the cassette of FIG. 37.

FIG. 40 is a front, partially broken elevational view of a receptacle useful in the present invention.

FIG. 41 is a side, partially broken elevational view the connection of a cassette of FIG. 37 with a receptacle of FIG. 40.

FIG. 42 is a perspective view of a flow cell useful in the present invention.

FIG. 44 is a perspective view of a diluent and waste container useful in the present invention.

FIGS. 46A–46E are schematic views showing a preferred relationship of the sample and intersample segments as useful in the present invention.

DESCRIPTION OF THE PREFERRED EMBODIMENT

Figure 1:
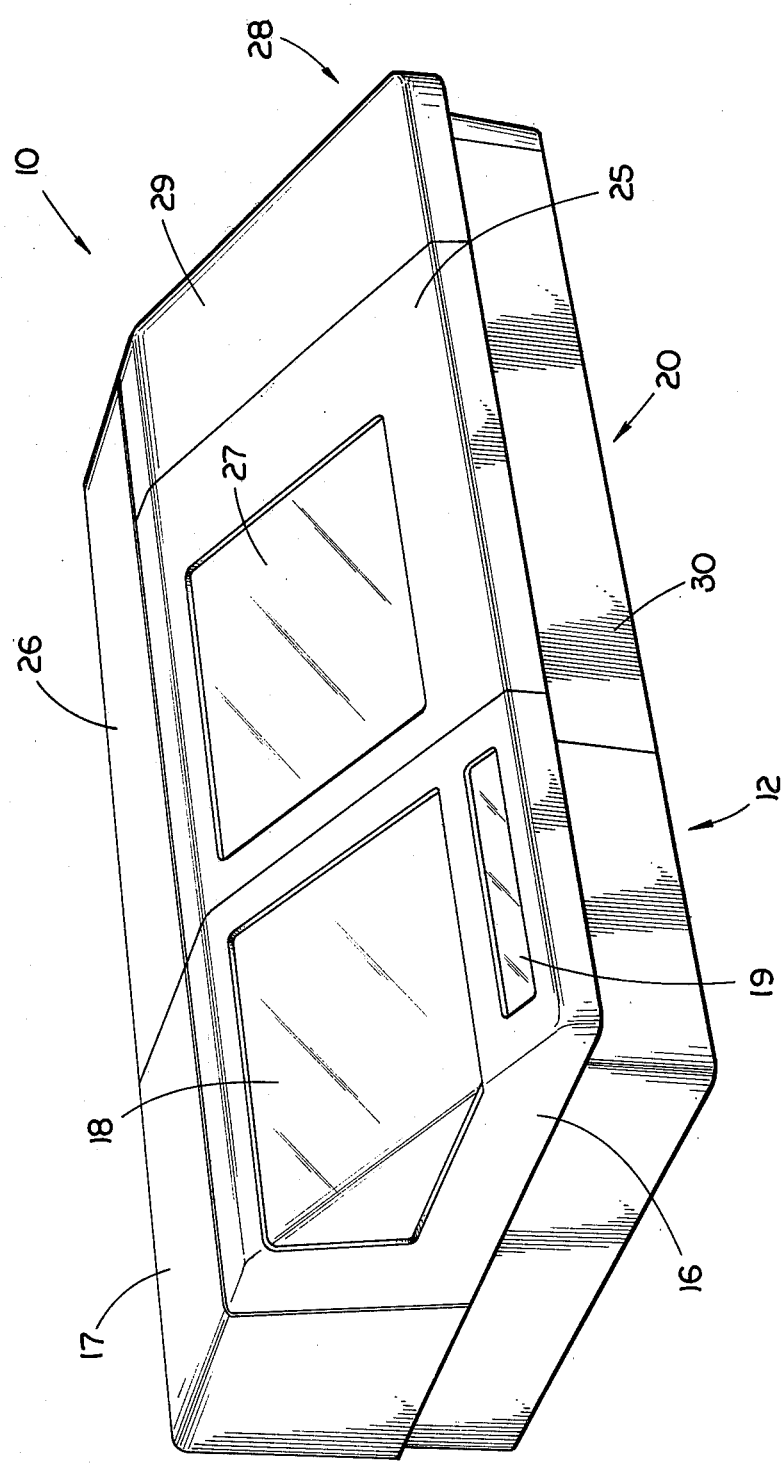
FIG. 1 is a perspective view of a chemical testing apparatus constructed in accordance with the present invention.
Figure 2:
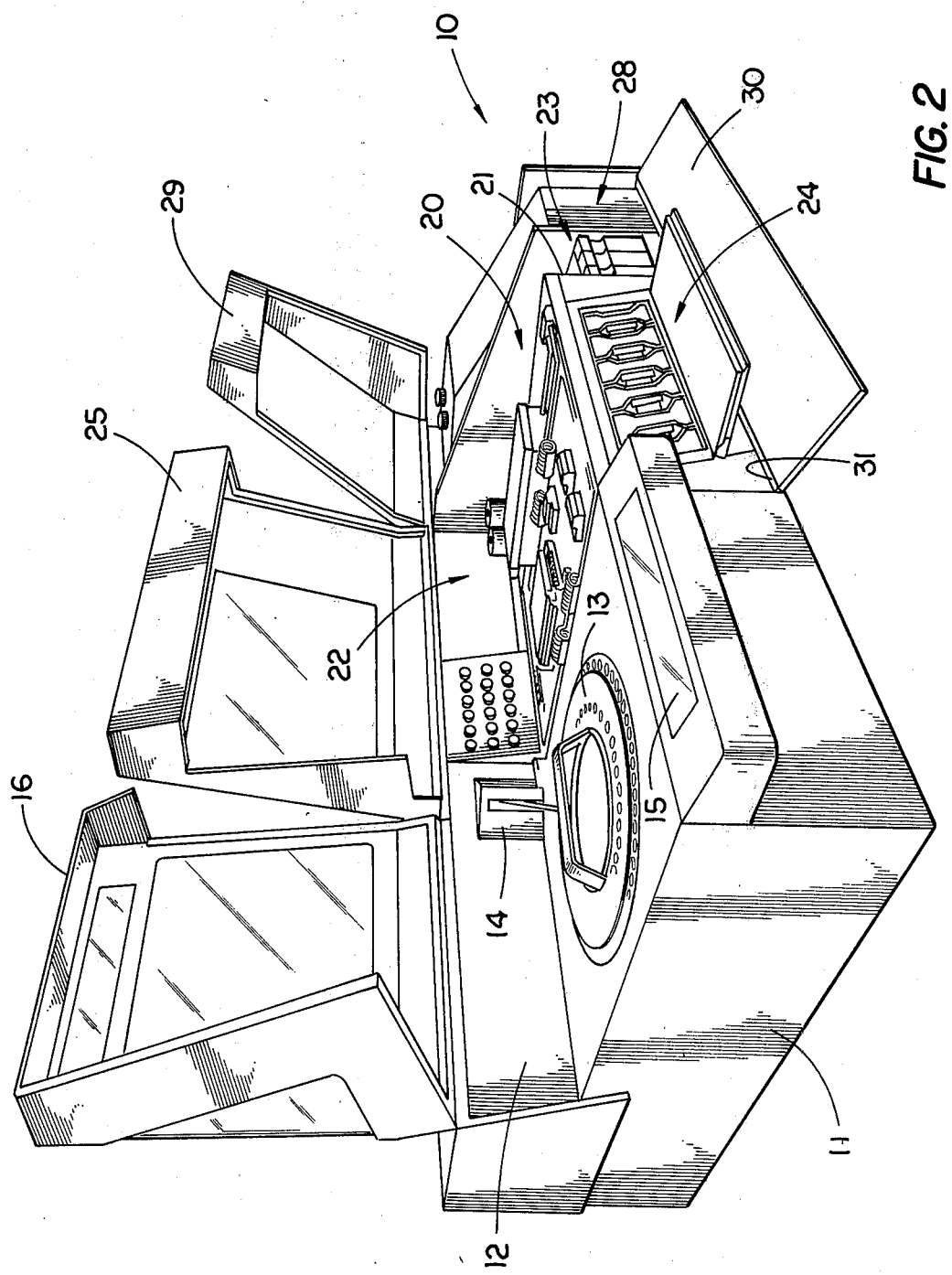
FIG. 2 is a perspective view of the apparatus of FIG. 1 with the covers open to reveal the inner details.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention relates to an automated chemical testing apparatus, particularly suited for use in the analysis of blood chemistry. In the broader sense, the present invention utilizes a continuous flow front end portion operatively coupled with an intermittent or discrete flow back end portion. The combination of the continuous and discrete flow portions provides particular advantages including a higher throughput and improved accuracy, all as will be further described below. Various changes or modifications to the continuous/discrete flow portions are contemplated, and are considered to fall within the purview of the present invention.

Preferably, the continuous flow portion introduces the sample material or standard material to the system and combines such material with suitable diluent and reagents to produce the desired chemical or physical reaction. As in typical continuous flow analyzers, the continuous flow portion of the present apparatus operates by pumping sample segments through small diameter tubing. In customary fashion, the successive sample segments are separated by intersample segments including liquid wash segments separated from the sample segments by air segments. For purposes herein, the terms sample and sample material are used to encompass both the unknown samples and known standards provided to the apparatus, except where it is clear from the context that only the unknown sample is intended. The term sample segment is used to refer to the liquid segment in the apparatus which contains either an unknown sample or a known standard. The term sample segment encompasses the entire liquid segment in which a sample or standard material is contained, and this includes diluent, buffer, reactants and reaction products when present.

The discrete flow portion preferably performs the chemical analysis or measuring of the reaction products in the sample segment. The reaction itself and separation of the reaction products, when desired, may occur during the continuous or discrete flow phases. Preferably the reaction takes place in the continuous flow portion and the separation of reaction products occurs in the discrete flow portion. Typically, the separation process may be accomplished more quickly than the time required to achieve the desired degree of reaction. Thus, the separation procedure is usually better suited to be accomplished in the discrete flow portion since the fluids generally move more quickly through the discrete flow portion as will be further described. The slower, reaction process can be more suitably accommodated in the continuous flow portion of the analyzer since this will not affect the throughput of the analyzer, as it would in the discrete flow portion.

The operation and use of continuous flow analyzers, without discrete flow portions as utilized herein, are known in much of the prior art, as is much of the technology and methodology associated therewith. It is therefore considered unnecessary to recite the common knowledge in the art relating to such devices and their operation. Details will be provided however, in order to provide a full and clear description and understanding of the present analyzer. For convenience and clarity, the present analyzer will be described herein with respect to the preferred embodiment of the device and its components, which comprises an automated radioimmunoassay (RIA) analyzer. It is to be understood, however, that the concepts and components specifically described are considered exemplary only. The application of the described concepts and the detailed components, as well as their equivalents, to other types of automated chemical testing apparatus is contemplated, as encompassed by the claims appended hereto.

The preferred RIA apparatus is operable for digoxin, thyroxine ($T_4$) and triiodothyronine (T3U uptake) tests. The digoxin test utilizes a competitive binding of the sample or standard digoxin and a $^{125}I$ labeled digoxin with the limited sites on a digoxin-specific antibody. The concentration of digoxin in the serum is inversely related to the amount of $^{125}I$ labeled digoxin bound to the antibody. The preferred embodiment of the present apparatus conducts this test by combining, in succession, a diluent segment, a digoxin-containing sample segment, a buffered $^{125}I$ labeled digoxin tracer segment and a digoxin antibody. This combined sample segment is passed through an incubator to provide a uniform, reproducible binding reaction. This sample segment is then preferably passed through a resin column which holds the sample digoxin and the $^{125}I$ labeled digoxin which has not become bound to the antibody. The antibody and bound digoxin is moved into a flow cell and the amount of $^{125}I$ labeled digoxin is determined and used to calculate the amount of digoxin present in the initial sample. The apparatus conducts the $T_4$ test by an analagous pathway. The T3U uptake test measures the relative saturation of the thyroxine binding proteins, primarily T6B. A buffered, $^{125}I$ labeled thyroxine tracer segment is combined with the mixed diluent and sample segment and incubated prior to separation out of the unbound thyroxine. The amount of tracer is then measured and used to determine the thyroxine binding capacity, i.e. relative saturation, of the binding proteins.

The preferred RIA analyzer comprises a microprocessor controlled, dual channel analyzer operable for thyroxine (T$_4$), triiodothyronine (T3U) and digoxin. This RIA analyzer utilizes $^{125}$I gamma radiation detection techniques. In accordance with the preferred embodiment to be described, the dual channel capacity refers to the ability to conduct two simultaneous tests, with a capacity of a typical maximum of forty specimens per hour. A first channel of the analyzer is provided to selectively conduct either T3U uptake or digoxin tests, while the other channel is operable to conduct T$_4$ tests. The microprocessor is preferably programmed to provide either single or duplicate sampling of each unknown sample and standard, with duplicate sampling being preferred unless indicated otherwise by the operator.

The microprocessor provides control functions for the system components. Further, the microprocessor is preferably programmed to provide additional warning and monitoring functions. A calculator/processor interfaces to the analyzer microprocessor to provide data reduction calculations and to print out results in the most preferred embodiment. Under the microprocessor control, the system is fully automated, simple to operate, low in cost and has a high throughput.

Referring in particular to the drawings, there is shown an automated continuous/discrete flow analyzer 10 constructed in accordance with the present invention. The chassis is suitably sized to have overall dimensions of 112 cm in length, 51 cm in width, and 29.2 cm in height. Analyzer 10 includes a chassis 11 generally partitioned into three sections. The sampling section 12 includes part of the continuous flow portion of the analyzer and houses the sample carousel 13 and sampling probe mechanism 14. A display panel 15 is located at the front of the sampling section and provides a digital display of the radiation counts obtained upon analysis of the samples. Sampling section cover 16 is hingedly mounted to rear panel 17 of the chassis and includes windows 18 and 19 to permit viewing of the sampling operation and display panel, respectively. In the closed position, as shown in FIG. 1, the sampling section cover 16 protects the components of sampling section 12, and further prevents contamination of the test samples, standards and wash liquid contained therein.

Chemistry section 20 encompasses a part of the continuous flow portion and also the discrete flow portion of the analyzer, and houses the majority of the handling, processing and analyzing components. The chemistry section is divided at wall 21 into the remainder of the continuous flow portion 22 and the discrete flow portion 23. The reagents and a cleaning solution are contained in the refrigerator 24 located at the front of the chemistry section. A chemistry section cover 25 is hingedly mounted to rear panel 26, and in the closed position, as shown in FIG. 1, operates to protect the chemistry section components from dust and damage and further prevents contamination of the test liquids. A window 27 is provided to permit observation of the chemistry section components, and particularly the fluid flow, while the chemistry section cover is in the closed position.

In the discrete flow portion (FIG. 3) of the chemistry section there are included the collection cups 251, the separation resin columns 264 received within complementary receptacles 279, and the flow cells contained within standard gamma radiation counters 397. Several valves 218 are interconnected (not shown) with these components to provide suitable coordination of the components and fluid flow, as will be further described below. The components are mounted upon a tray 398 including a collector pan portion 399 to receive spilled or leaked liquids.

A liquid storage section 28 houses containers for the diluent and wash solutions, which typically are one and the same, and for the system waste liquids. Liquid storage section 28 is provided with a cover 29 which is hingedly mounted to the rear panel 26 to provide access to these containers. A front panel 30 extending the width of the chemistry and liquid storage sections is hingedly mounted to the bottom 31 to further provide access to these containers and to portions of the chemistry section 20 such as refrigerator 24.

The analyzer 10 in its preferred embodiment as described herein comprises a number of primary and secondary mechanical components, as well as suitable electronics to operate, coordinate and monitor such components. The components and their various functions and interrelations within the analyzer will be described in detail, but first an overall description of the system will be provided for clarity.

In general, the present apparatus includes a continuous flow means which provides a substantially continuous flow stream of alternating sample and intersample fluid segments. The term continuous is used herein as referring to an essentially uninterrupted flow, typically through a tube, and is intended to cover as well an intermittent flow of the type produced by peristaltic pumps when the result is substantially continual flow. The apparatus further includes collecting means for collecting the sample segments separate of the intersample segments, and discrete flow means for alternately flowing the collected sample segments and the intersample segments to an analysis means and a waste collection means, respectively.

More specifically, in the preferred embodiment the standards and the unknown test samples are contained in sample cups received within an indexing sample carousel. The sample carousel 13 is removably mounted within sampling section 12 and is operable to rotate to position the sample cups as required for sampling. A wash cup providing a source of wash liquid is located adjacent the carousel. Sampling probe mechanism 14 includes a sample probe which is connected with a peristaltic pump. The sample probe selectively alternates between the standards, test samples and wash to withdraw liquid segments separated by intersegment air bubbles.

These fluid segments are moved by the peristaltic pump to the various components of the continuous flow portion of the analyzer. This initial or sample stream is combined with a diluent stream and one or more reagent streams to provide the desired reaction mixture. This mixture is preferably incubated during a portion of its continuous flow phase and is then delivered into collection cups. The collection cups alternately collect the sample and intersample segments which are moved by a discrete flow means, preferably a vacuum pump, to a separation unit and waste container, respectively. In the particular embodiment described herein, the analyzer performs radioimmunoassay procedures and the preferred separation method is a resin column through which the reaction products are passed. The desired effluent from the resin column is then passed into a flow cell for counting and eventually to waste. A more detailed description of the analyzer components will follow.

A sampling means is provided for drawing the standards, samples, wash and air into the apparatus. The sampling means may assume a variety of configurations, and generally may include the various sampling means presently used with continuous flow testing apparatus. The sampling means of the present apparatus preferably includes a sample carousel received upon a carousel indexing means and carrying several standards and samples in individual cups or other receptacles. A sampling probe mechanism is preferably movable among the standards, samples and a separate wash solution receptacle for withdrawing portions of each into the apparatus.

Figure 4:
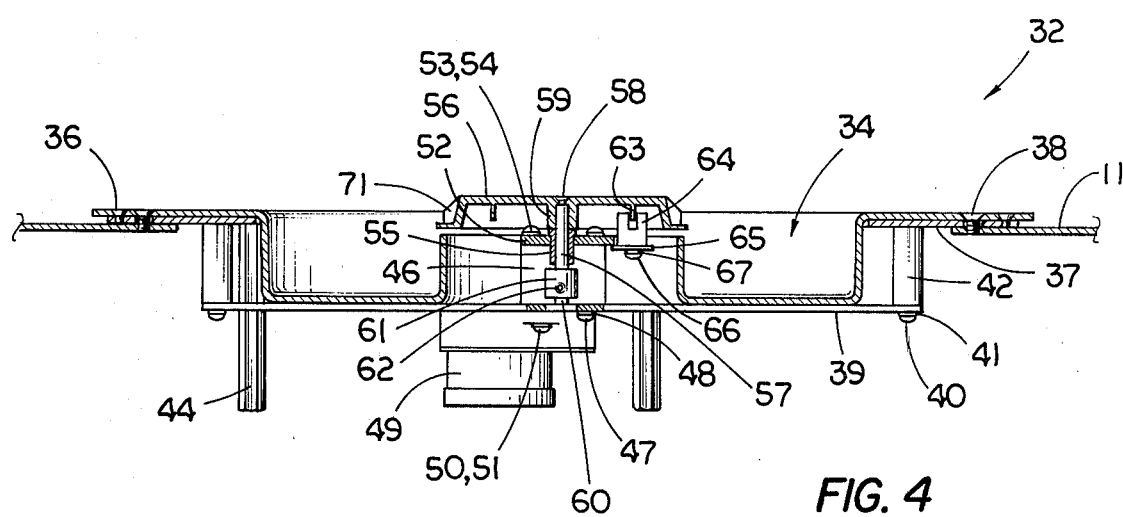
FIG. 4 is side, cross-sectional view of a carousel drive assembly useful in connection with the present invention.
Figure 5:
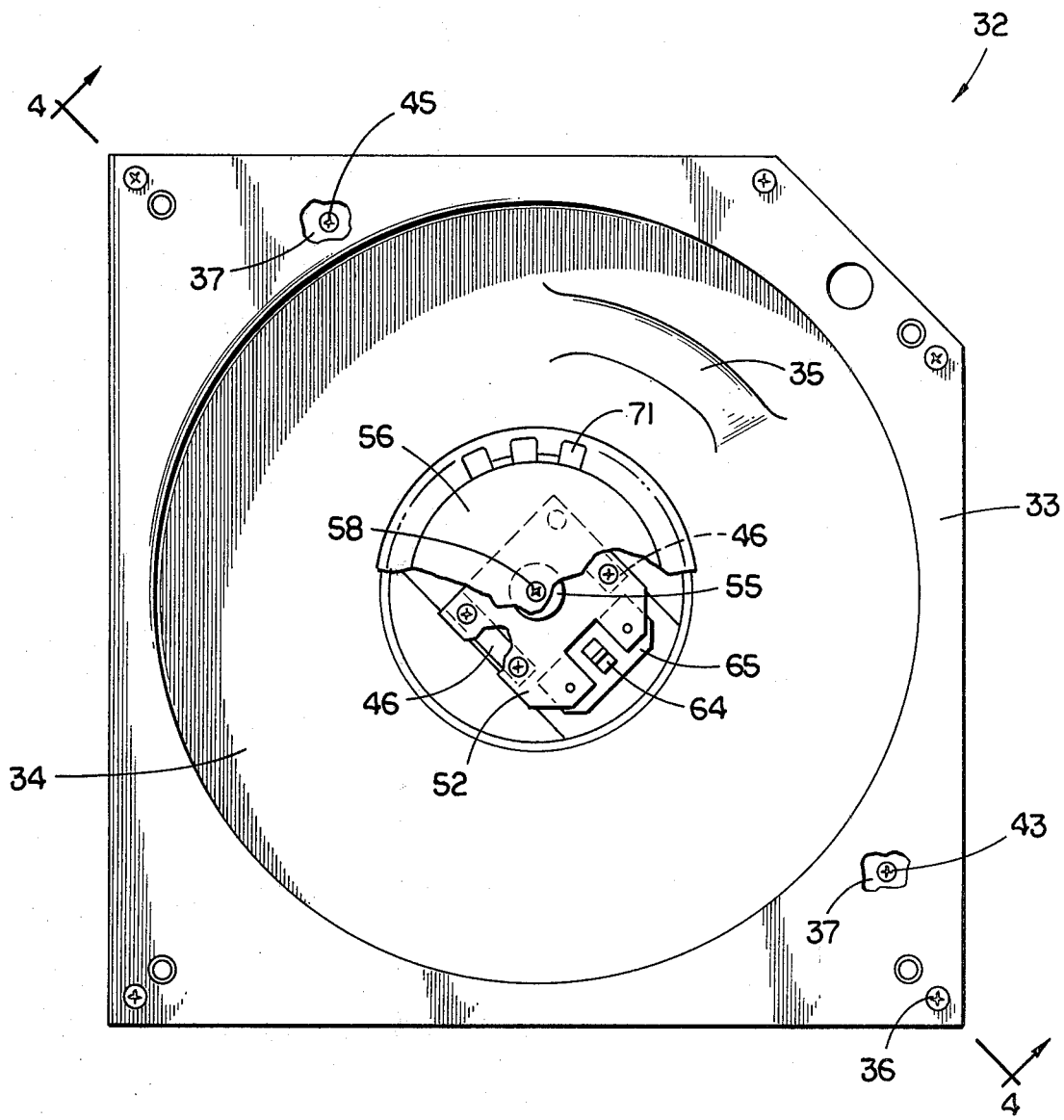
FIG. 5 is a top, plan view of the carousel drive assembly of FIG. 4.

The sampling means includes an indexing means for indexing the carousel through various sampling positions. Referring in particular to FIGS. 4 and 5, there is shown a carousel drive assembly 32 useful in connection with the present analyzer. FIG. 5 is a top, plan view of the carousel drive assembly and FIG. 4 is a side, cross-sectional view of the assembly of FIG. 5, taken along the line 4—4 in FIG. 5 in the direction of the arrows. Assembly 32 includes a spill cover 33 generally square in shape and having a chamfer. Spill cover 33 defines an annular channel 34 which includes a concentric, centrally-positioned, upraised portion 35 along a part of the annular channel. The upraised portion 35 is provided to permit the use of photodetectors to assess the presence of sample cups and the rotational position of the carousel, as will be more fully described in respect to FIGS. 8 and 9.

Spill cover 33 is secured by screws 36 to a doubling plate 37, and both are in turn secured to chassis 11 by screws 38. A flat, rectangular motor mount plate 39 is secured by means of screws 40 and split lock washers 41 to motor plate blocks 42, which are in turn secured to doubling plate 37 by screws 43. Support legs 44 are similarly secured to doubling plate 37 by screws 45.

Bearing plate blocks 46 are mounted to the motor mount plate 39 by means of screws 47 and split lock washers 48. A synchronous motor 49, such as a Hurst, model no. A-6 motor, is mounted to motor mount plate 39 by means of screws 50 and split lock washers 51. Additionally, screws 50 extend through the motor mount plate and secure the bearing plate blocks thereto. Bearing plate 52 is secured to the bearing plate blocks 46 by means of screws 53 and split lock washers 54. Bearing 55 is received within an aperture defined by bearing plate 52 and includes an annular shoulder which rests upon the upper surface of bearing plate 52. The carousel drive wheel 56 is secured to shaft 57 by means of screw 58. Shaft 57 is received within a central aperture defined by bearing 55, and the cylindrical projection 59 from carousel drive wheel 56 rests upon the upper surface of bearing 55. Shaft 57 is secured to the shaft 60 of motor 49 by means of a collar 61 and set screw 62.

In accordance with the described construction, the analyzer is provided with a carousel drive wheel upon which the sample carousel is received, and a spill cover 33 is positioned to protect the underlying components from spilled or other foreign material. The carousel drive wheel is directly coupled with a synchronous motor 49 to rotate the carousel drive wheel 56 and therefore the carousel to the desired positions. Various other means exist in the art for providing an indexed rotation of a sample carousel, and these would be suitable for use in conjunction with the present analyzer. The described construction is preferred, however, particularly for its simplicity and reliability of design.

Motor 49 is microprocessor controlled to selectively index the carousel drive wheel to each of the several positions at which the unknown test samples or standards are received. Radially aligned with each of the test sample positions is a downwardly-extending flag 63. A photodetector 64 is mounted upon plate 65 which is secured to the bearing plate 52 by means of screws 66 and split lock washers 67. Photodetectors useful in this analyzer for detecting sample cups and flags are readily available, and include the Clairex Electronics, Inc. photodetector CLED-1 (light emitting diode) and CLR-2170 (phototransistor). In customary fashion, the photodetector is thereby positioned such that each of the flags 63 is received within the photodetector channel between the photodetector elements, the light emitting diode and the opposed phototransistor. The photodetector thereby detects when a flag has moved into the position within the photodetector and this information is utilized by the microprocessor to control the synchronous motor 49 and therefore the position of the sample carousel. A suitable motor 49 for use in the present analyzer is a Hurst A-6 synchronous motor.

The carousel indexing means, perferably comprising the described carousel drive assembly, is operable to index the sample carousel to position the unknown test samples and/or standards in the manner and for the time desired for sampling. For the described analyzer, the sampling time for an unknown test sample or a standard is approximately sixty seconds, during which time the sample draw is about 0.160 milliliters. Under these parameters, the sample carousel may be indexed to receive forty samples and/or standards per hour.

Figure 6:
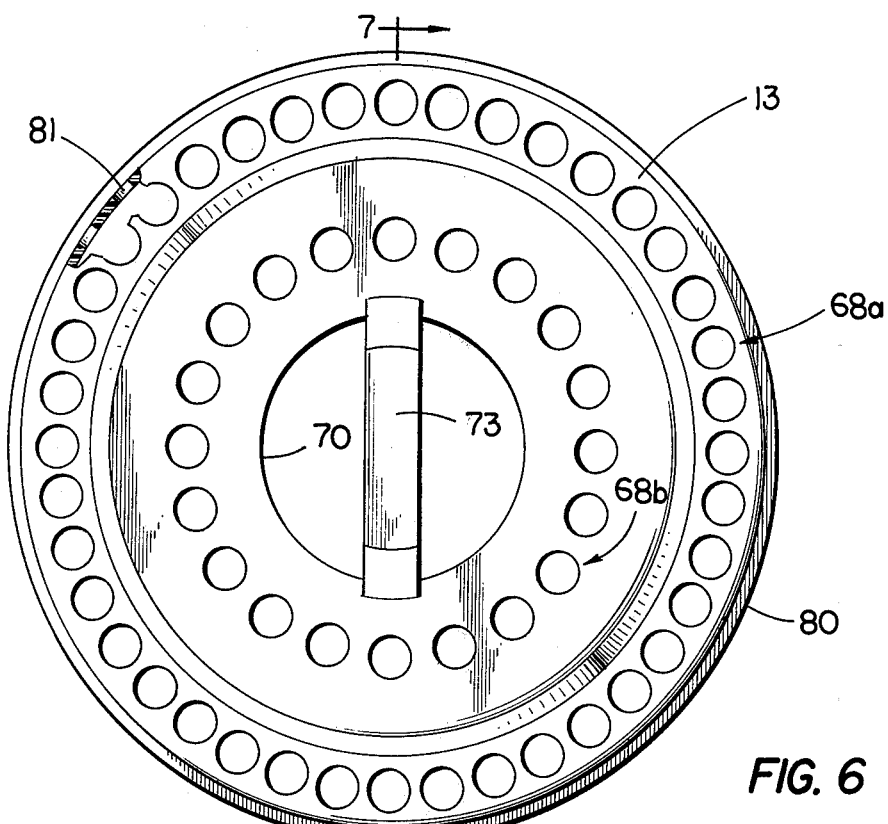
FIG. 6 is a top, plan view of a sample carousel useful in the present invention.
Figure 7:
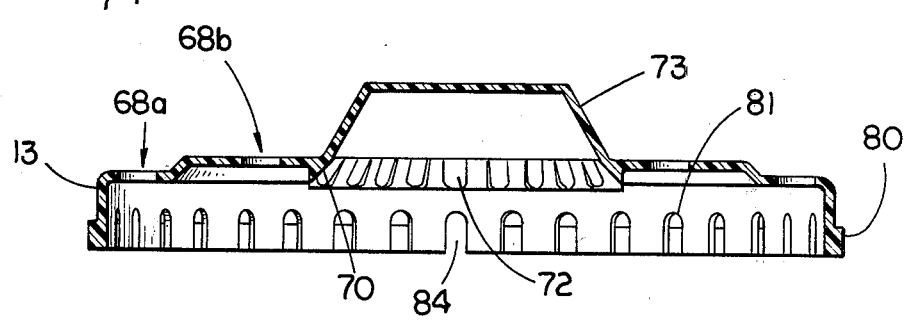
FIG. 7 is a cross-sectional side view of the carousel of FIG. 6.
Figure 8:
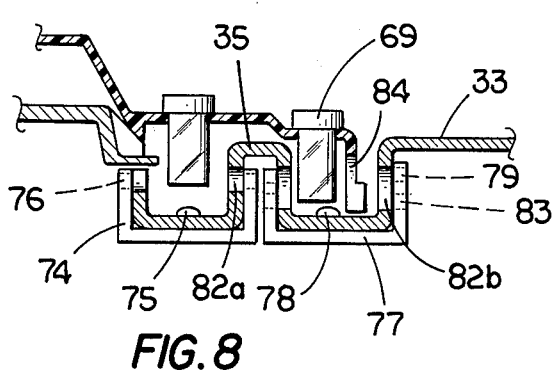
FIG. 8 is partial, cross-sectional side view of the carousel of FIG. 6 mounted upon the carousel drive assembly of FIG. 4.
Figure 9:
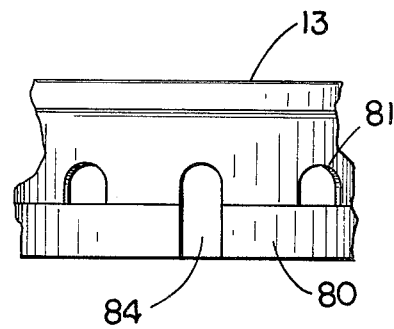
FIG. 9 is a partial, side elevational view depicting details of the carousel of FIG. 6.
Figure 11:
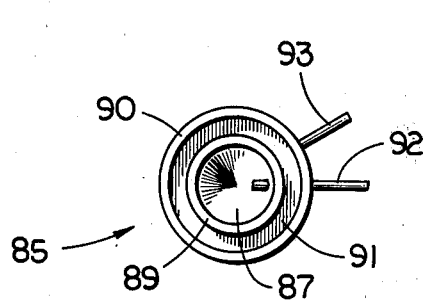
FIG. 11 is a top, plan view of the wash cup of FIG. 10.
Figure 10:
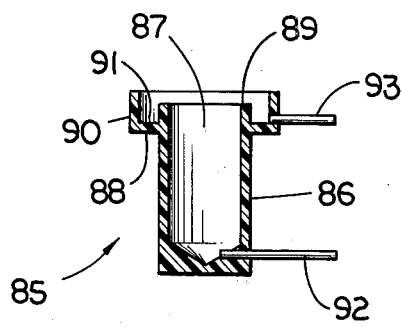
FIG. 10 is a side, cross-sectional view of a wash cup useful in connection with the present invention.
Figure 12:
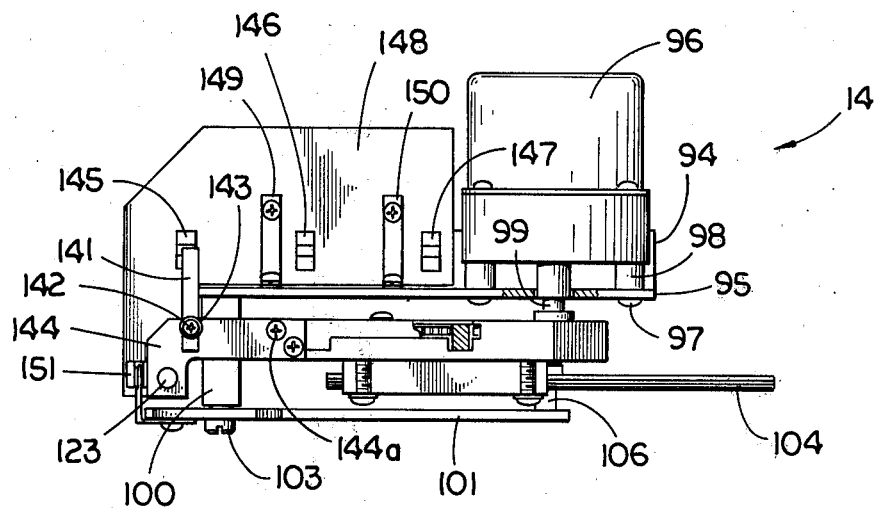
FIG. 12 is a top, plan view of a sampling probe mechanism useful in accordance with the present invention.

A preferred construction of a sample carousel 68 useful in conjunction with the present analyzer is shown particularly in FIGS. 6–9. FIG. 6 is a top, plan view of the sample carousel and FIG. 7 is a cross-sectional side view of the carousel of FIG. 6 taken along the line 7—7 in FIG. 6. FIG. 8 is a partial, cross-sectional side view of the carousel mounted upon the carousel drive assembly. FIG. 8 together with the partial side elevational view of FIG. 9 depict the carousel details relating to the photodetector operation respecting detection of sample cups and carousel position.

Sample carousel 13 defines an outer row 68a and an inner row 68b of circular holes within which sample cups 69 (FIG. 8) are received. Carousel 13 is preferably shaped to have the outer row of sample cups held at a position lower than the inner row of cups, as shown in FIG. 8. It will be appreciated, however, that the configuration of the carousel may suitably have a variety of shapes, as may the sample cups and the holes within which they are received. In a particularly preferred embodiment, the carousel has a diameter of approximately ten inches and carries forty sample cups in the outer row 68a for unknown test samples, and twenty sample cups in the inner row 68b for standards and the like. Suitable cups are readily available, and include the standard 1.8 cc and larger cups by Evergreen Scientific of Los Angeles, Calif. The cups suitably are sterile, disposable plastic cups.

Carousel 13 includes a central, annular portion 70 which is received upon the carousel drive wheel 56.

Means are provided to align the sample carousel 13 upon the carousel drive wheel 56 to coordinate the positions of the sample cups with the positions of the flags 63, thereby assuring proper indexing of the carousel. Such means may assume a variety of forms, and conveniently comprises a plurality of projections 71 (FIGS. 4 and 5) on carousel drive wheel 56 which are received in complementary shaped recesses 72 in the underside of the annular portion 70 of the sample carousel. The circular holes of the outer row 68a are each preferably aligned with one of the holes in the inner row 68b, and the recesses 72 (FIG. 7) may be conveniently positioned to be associated with each of the holes of the inner row. Sample carousel 68 also includes a handle portion 73, preferably molded integrally with the carousel, to facilitate handling of the carousel.

The radial positioning of the sample carousel is controlled in one aspect by the microprocessor response to information received from the photodetector 64, which as previously indicated controls the synchronous motor 49 in customary fashion. In addition, photodetectors are used to determine whether a sample cup is contained within a particular sample cup hole. For this reason, the previously described upraised portion 35 (FIGS. 5 and 8) in spill cover 33 is provided. Referring in particular to FIGS. 8 and 9, it is shown that a photodetector 74 having a set of photodetector elements 76, including opposed light emitting diode and phototransistor, is secured to the spill cover 33 by screws 75. The photodetector 74 is thereby positioned to straddle the apertures 82a (FIG. 8) provided in spill cover 33 and the inner row of sample cups as the carousel is rotated. As the carousel is successively indexed, the photodetector elements 76 will sense whether a sample cup is positioned within its detecting path, through apertures 82a, and this information is provided to the microprocessor. Thus, sampling of the standards or other materials contained in the inner row of sample cups is performed only when a sample cup is present in a particular sample cup hole positioned for sampling.

Similarly, a photodetector 77 is secured to spill cover 33 by screws 78, and is positioned to have a first set of photodetector elements 79 straddle the outer row of sample cups as the carousel is rotated. The rim portion 80 of the sample carousel is provided with apertures 81 (FIGS. 6 and 9) for each of the sample cup holes in the outer row. As the carousel is indexed, each successive aperture 81 is brought into alignment with the apertures 82b in spill cover 33 adjacent photodetector 77. The first set of photodetector elements 79 is thereby enabled to determine the presence of a sample cup in the associated sample cup hole. Again, this information is provided to the microprocessor to provide for sampling the outer row stations only when a sample cup is present.

In addition, photodetector 77 includes a second set of photodetector elements 83. Elements 83 are positioned below the first set of elements 79. This second set of photodetector elements is used to assess the radial position of the carousel relative the spill cover. As shown particularly in FIG. 9, there is provided one aperture (corresponding generally with apertures 81) which extends fully to the edge of rim portion 80 to form essentially a slot 84 at that location. This slot 84 includes a portion corresponding to apertures 81 to permit the photodetector elements 79 to detect the presence of a sample cup in the associated sample cup hole. In addition, the slot permits the second set of photodetector elements 83 to ascertain when the carousel is in the position to align the slot 84 in the sensing path of the elements 83.

In this preferred embodiment, the slot 84 is positioned in the carousel to indicate the proper position of the carousel for initiating an analysis of standards and/or unknown test samples. Under appropriate microprocessor control, upon initiating an analysis run the carousel will successively index until it has been positioned with the desired first position located as the first sampling station. In typical operation, any standards to be run are proceeded with first, and after indexing to the starting position the carousel will index through each position for the standards. Following the sampling of standards, the carousel indexes through each position of the test samples. It has been found to be preferable that the slot 84 is positioned (relative the desired start position of the carousel to initiate a given run) such that after the carousel has indexed to the position of the slot 84 then the carousel is indexed one more position to initiate a run.

For sampling the standards, the carousel will, for example, proceed to index to each position in which a sample cup is contained in the inner row 68b, all as indicated by operation of the photodetector elements 76 in conjunction with the general indexing mechanism utilizing photodetector 64. Upon completing this initial run, the carousel will successively index to each position for which a sample cup is found in the outer row 68a, as indicated by operation of the photodetector elements 79 again in connection with the general indexing mechanism associated with photodetector 64.

Wash liquid means are included to provide wash liquid to the apparatus. Various means may be used and are contemplated herein. For example, a separate wash liquid pump line could be included which directly pumps the liquid into the sample probe line. Preferably, a wash cup 85 is located adjacent the sample carousel. The wash cup is filled with an appropriate wash liquid and provides the wash liquid as part of an intersample segment. The wash liquid thus operates efficiently and effectively to prevent carry over from one sample to the next, and should as a result be an inert material. Various fluids are known in the art for this type of application and such are useful in the present apparatus. The wash fluid is preferably the same as the diluent solution.

Wash cup 85 includes a central, cylindrical portion 86 defining a fluid reservoir 87. A shoulder 88 extends outwardly of the cylindrical portion 86 from below the top edge 89 of the cylindrical portion. A cylindrical wall 90 extends upwardly from shoulder 88 above the top edge 89, thereby defining an overflow channel 91 surrounding the top of the wash cup. A reservoir tube 92 is mounted to cylindrical portion 86 and communicates with the fluid reservoir 87. An overflow tube 93 is secured to the wash cup through wall 90 and communicates with the overflow channel 91. Reservoir tube 92 is connected with a suitable fluid source and operates under appropriate pump means to fill the fluid reservoir. The reservoir continuously receives fluid and the excess fluid passes over the edge 89 and into the overflow channel 91 from which it is removed through overflow tube 93, preferably by a vacuum pump connected to a suitable waste container.

As will be more fully described below, the analyzer includes a sampler probe which extracts standards and samples from the sample cups and wash solution from the wash cup. Wash cup 85 provides a fluid reservoir 87 from which the sample probe obtains the wash solution segments. The continuous flow of fluid through reservoir 87 is advantageous in at least two respects. Generally, the sampling probe alternates between the sample cups (of standards or unknown test samples) and the wash cup. The fluid motion in the wash cup operates to cleanse the tip of the sample probe of the test sample or standard which may be present on the probe. Second, any traces of test samples or standards which are washed into the fluid in the wash cup are continuously diluted and removed. Thus, the wash fluid segments are maintained highly devoid of other components, and the function of the wash fluid to separate and cleanse between successive samples is enhanced.

Sampling probe means are provided for moving sample, standard and wash into the apparatus. Various sample probe mechanisms are known in the art and are useful with the present apparatus. The sample probe mechanism provides a means for withdrawing samples, standards and wash solution into the apparatus. A preferred sampling probe mechanism 14 is shown particularly in FIGS. 11-20 E, and as shown is operable to extract either sample, standard or wash solution as required. The sampling probe mechanism 14 includes a mount plate 94 secured to the chassis (not shown) and connected with motor mount plate 95. Motor 96, such as an A. W. Haydon model no. K86113-44 motor, is secured to the motor mount plate 95 by bolts 97 received through apertures in the motor mount plate and through spacers 98. The motor mount plate defines an aperture within which the motor shaft 99 is received. A suitable motor for this application is the North American Phillips, 100 rpm motor having designation K6 113-U4.

Also secured to the mount plate 94 and motor mount plate 95 is a probe mount block 100. Each of a pair of arms 101 is secured to the probe mount block 100 as particularly shown in FIG. 14. Arm 101 (FIG. 14) includes an aperture within which bearing 102 is press fit. Shoulder screw 103 is received through bearing 102 and is threadingly received by the probe mount block 100. The opposite ends of arms 101 are pivotally mounted to slide 104. For each of the arms 101, a bearing 105 is press fit within an aperture defined by slide 104, and a spacer 106 is positioned between the bearing and the arm. A shoulder screw 107 is received through bearing 105 and spacer 106 and is threadingly received within arm 101. The attachment points for each end of the two arms are located to define a parallelogram, whereby the horizontal orientation of slide 104 is maintained during pivoting of the arms and therefore during vertical displacement of the slide.

Carriage 108 is mounted to ride upon slide 104. A pair of guide wheels 109 are secured to carriage 108. For each guide wheel, a bearing 110 is press fit into the guide wheel and a spacer 111 is positioned between the bearing and carriage 108. A shoulder screw 112 is received through bearing 110 and spacer 111 and is threadingly received within carriage 108. The guide wheels define a generally V-shaped guide channel within which the complementary-shaped edge of slide 104 is received. A guide 113 is mounted to the carriage 108 by screws 115 and washers 114. Guide 113 defines a generally V-shaped channel within which the complementary-shaped top edge of slide 104 is received. It will be appreciated that the mounting of arms 101, slide 104 and carriage 108 provide the carriage with ready mobility in both horizontal and vertical directions. Moreover, orientation of carriage 108 is maintained while movement occurs in vertical and horizontal directions.

Figure 16:
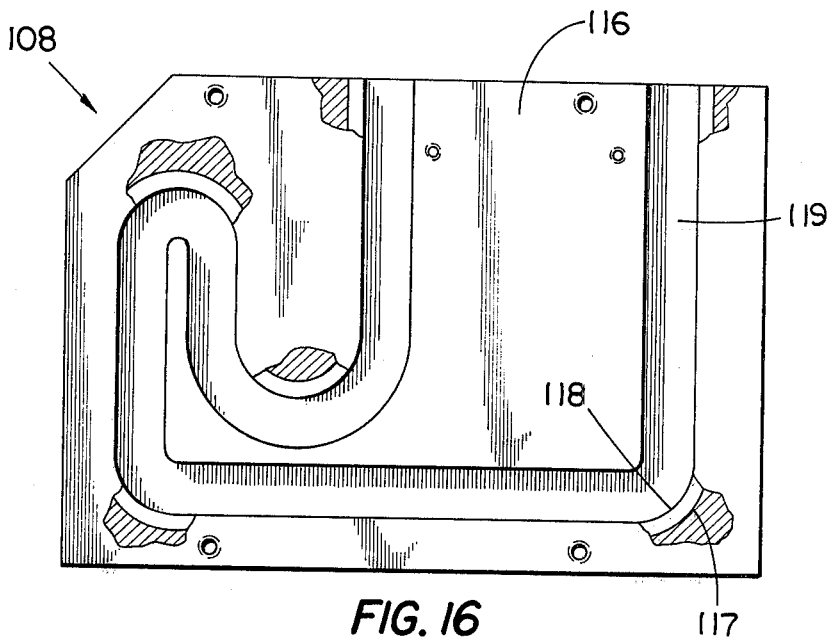
FIG. 16 is a side elevational view of the carriage used in the mechanism of FIG. 12.
Figure 15:
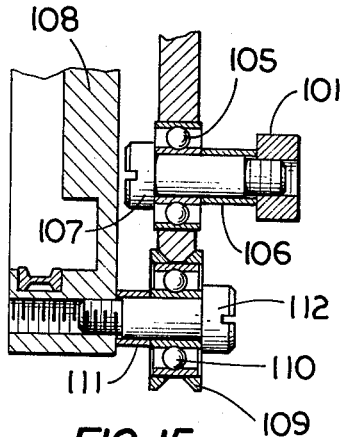
FIG. 15 is a partial end cross-sectional view showing the mounting of the slide to the carriage.
Figure 17:
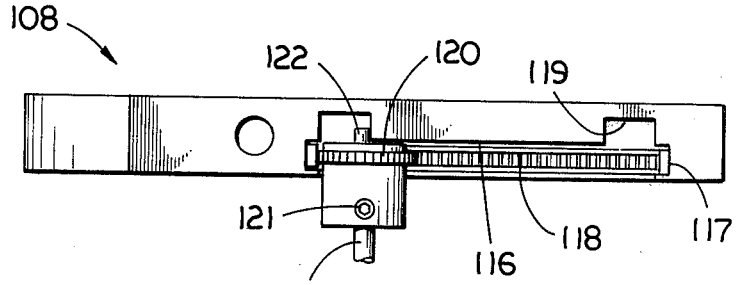
FIG. 17 is a top, plan view of the carriage and showing the connection therewith of the motor shaft gear.
Figure 18:
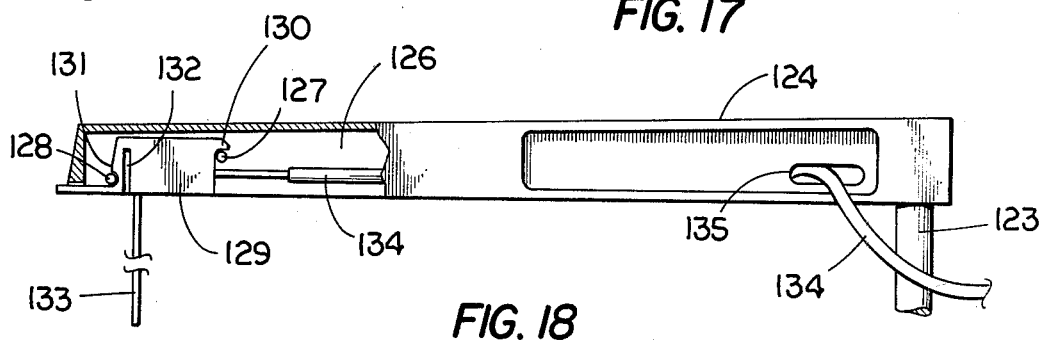
FIG. 18 is a side, elevational view of a sample probe arm useful in the present invention.
Figure 19:
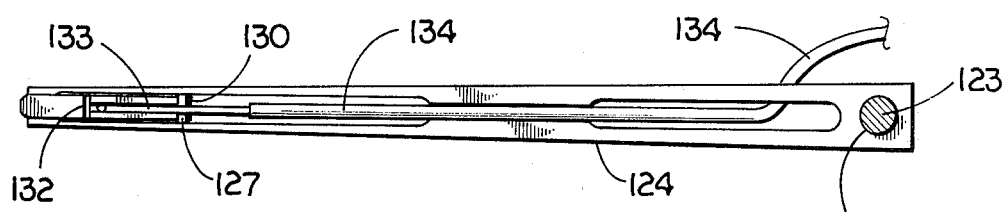
FIG. 19 is a bottom, plan view of the simple probe arm of FIG. 18.

As particularly shown in FIGS. 16 and 17, carriage 108 defines a recess 116 having a groove 117 extending about its outer perimeter. Fitted into the groove 117 is a slotted track 118. Recess 116 further includes a channel 119 extending along the outer perimeter of the recess. A gear 120 is mounted by set screw 121 to the motor shaft 99. Gear 120 is positioned along the motor shaft to align with and to engage the track 118, and further the end 122 of the motor shaft is received within channel 119. The end 122 of the motor shaft engages the channel 119 on the side opposite the track 118, thus holding the gear 120 adjacent to and engaged with the track.

From the above description, it will be apparent that operation of motor 96 and therefore gear 120 will cause the carriage 108 to move in correspondence to the shape of channel 119 and track 118. The configuration of the track and channel provide the desired movement of carriage 108, and therefore of the sample transfer probe mounted thereon.

Sample probe post 123 (FIG. 13) is mounted to the probe mount 144. The probe post is received within an aperture in the probe mount and is vertically adjustable by means of a set screw (not shown) which engages the post. Axial adjustment for the probe post (i.e., radially to the carousel) may be similarly provided, or more simply the relative position of the sample probe in the probe tube holder 129 may be adjustable for this purpose. Sample probe arm 124 (FIG. 18) defines an aperture 125 (FIG. 19) in which the upper end of post 123 is received. Sample probe arm 124 defines an interior channel 126, and a pair of pins 127 and 128 span thereacross. Probe tube holder 129 is received within the channel 126 and snap fits against the pins 127 and 128. Holder 129 includes a first projection 130 which is received between pin 127 and the interior wall of the sample probe arm. Upon insertion of projection 130 in this position between pin 127 and the wall of the sample probe arm, the probe tube holder 129 may be pivoted into the channel 126 and projection 131 snapped into position behind pin 128. In order to obtain this snap fit, the probe tube holder is preferably made from a resilient material, and a slot 132 is provided to facilitate this procedure. In addition, the probe tube holder 129 projects forwardly from the end of the sample probe arm, thus providing a means to grip the probe tube holder and remove it from the channel as required.

The probe tube 133 is secured within a longitudinal slot in the probe tube holder 129, such as by a suitable adhesive. The probe tube may comprise stainless steel or other suitable compositions. A tube 134 is coupled with the probe tube 133 and extends through channel 126 and out a side aperture 135 in the sample probe arm. In prior devices, the probe arm typically has included a molded in or clamped cartridge containing the probe tube. The present design advantageously utilizes a snap fit cartridge which is quickly and easily removed and installed without the need for tools.

As gear 120 rotates, the carriage is moved correspondingly to the configuration of the track. Particular positions of the carriage, and therefore of the probe tube, are shown somewhat schematically in FIGS. 20A-E. As shown in FIGS. 20A-E, the track configuration is selected to correspond to the positions of sample, standard and wash cups in which the probe tube is to be placed. It will be appreciated that the positions of these cups may be varied and that a similar variation in the track configuration would correspondingly be made.

Shown in the various views of FIG. 20 is the operation of the sampling probe mechanism with respect to the sample and wash cups to withdraw standard, sample, wash solution and air into the apparatus. The positions of the standard cup 136, sample cup 137, wash cup 138 and gear 120 remain generally the same relative one another. However, operation of the gear will cause the carriage to move and to therefore carry with it the probe tube 133. The present apparatus provides a flow stream in the flow path of the apparatus which has alternating sample and intersample segments. The term intersample segment is used herein to encompass the entire and various liquid and gas segments in the flow path intermediate the sample segments. As subsequently described, the intersample segment comprises a leading air segment as the leading end portion of the intersample segment, the leading air segment thus being adjacent the preceding sample segment. The intersample segment further includes a following air segment as the trailing end portion of the intersample segment, the following air segment therefore being adjacent the subsequent sample segment. The intersample segment also comprises one or more wash liquid segments intermediate the leading and following air segments. Where more than one wash segment is employed in a given intersample segment, the wash segments are typically and preferably separated by additional air segments.

Figure 20A:
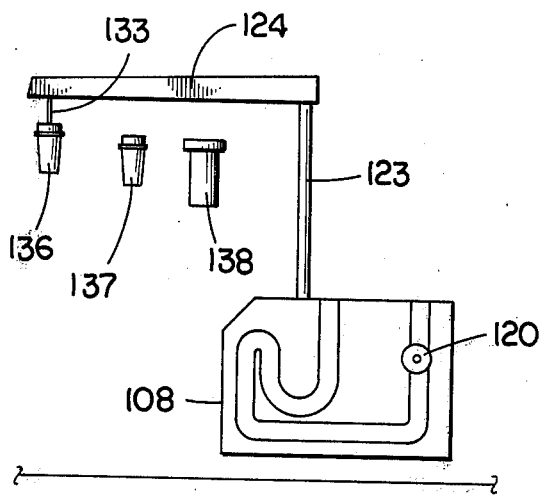
FIGS. 20A-20E are schematic view showing the various positions of the sample probe arm and mechanism with respect to the sample and wash cups.

In FIG. 20A the carriage is shown in a first, sample draw position in which the probe tube 133 is received within standard cup 136. Probe tube 133 is connected with pump means such as a peristaltic pump which causes the standard solution to be withdrawn through probe tube 133 in the position of FIG. 20A. Under appropriate microprocessor control, gear 120 is then caused to be rotated by the motor 96 to move the carriage through the intermediate, air draw position of FIG. 20B to the wash draw position of FIG. 20C. While in the air draw position, between the standard draw and wash draw positions, the probe tube 133 (FIG. 20B) is in the air, and the pump means therefore causes air to be drawn into the tube. In this manner, a leading air segment is introduced into the tube which will provide a division between the standard segment previously withdrawn and the wash segment about to be withdrawn.

Figure 20B:
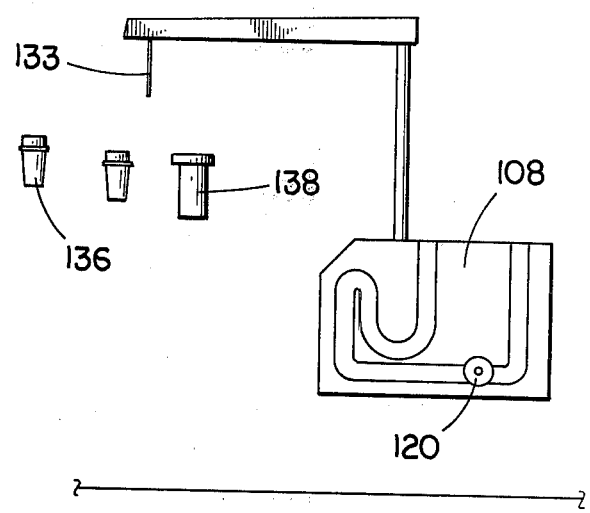
Figure 20C:
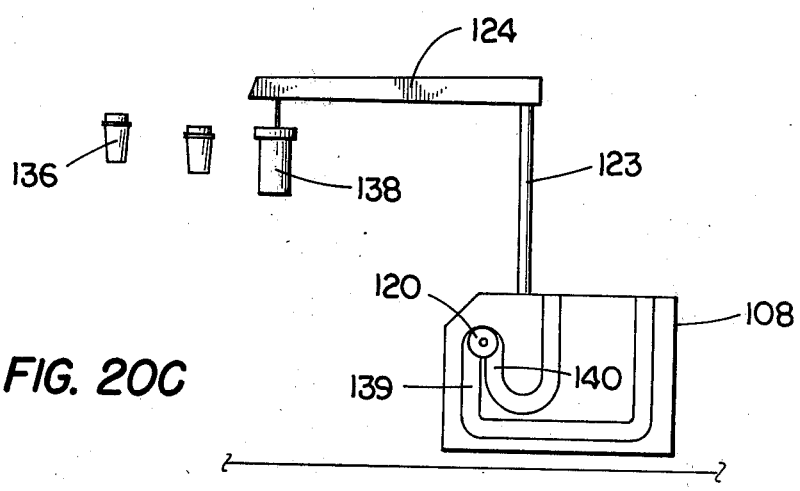

In the wash draw position of FIG. 20C, a segment of wash is withdrawn into the tube. It is considered advantageous to provide in a given intersample segment a plurality of wash segments with air segments therebetween. This is readily accomplished by rotating gear 120 sufficiently to move the gear relative either channel portion 139 or channel portion 140 (FIG. 20C) to withdraw probe tube 133 from the liquid in the wash cup 138, and then to return the probe tube into the wash liquid. The timing for this may be controlled as desired, and preferably the probe tube is moved into and out of wash cup 138 in several one second intervals.

Figure 20D:
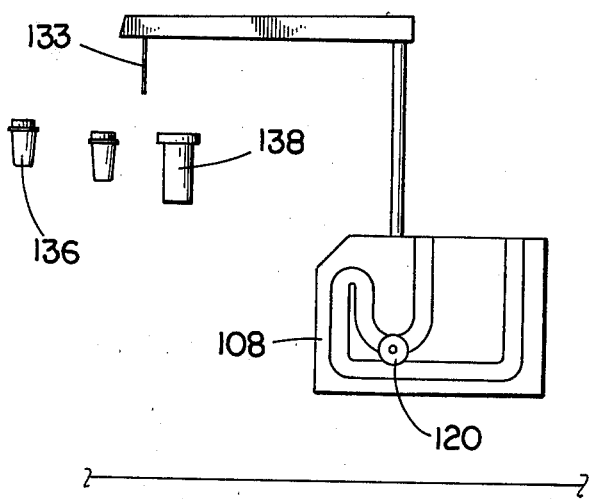
Figure 20E:
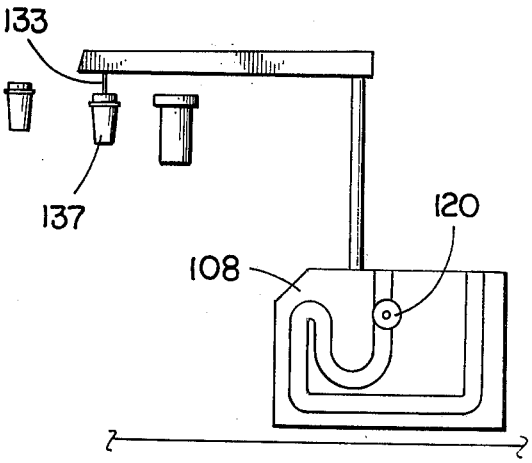

Gear 120 is then caused to rotate to move the carriage and associated probe tube through the intermediate air draw position of FIG. 20D to the sample draw position of FIG. 20E. Again, while passing between the wash draw position and the sample draw position the probe tube is carried through the air and a following air segment is introduced between the last wash segment and the subsequent sample. While in the position of FIG. 20E, a segment of a subsequent sample is withdrawn into the probe tube 133 and thereby introduced into the system.

It will be appreciated that the duration for the probe tube being maintained in any of the described positions can be controlled as desired. Further, the cycling of the various positions may be controlled as desired to provide standard, sample, wash and air segments to the probe tube in the amounts and arrangements desired. For example, a plurality of standard or sample segments may be consecutively introduced simply by moving the probe tube into and out of the standard or sample cups a plurality of times before moving the tube to the wash cup. Similarly, a great variety of arrangements can be achieved by the appropriate combination and ordering of the various positions for the sample probe.

The present apparatus utilizes a plurality of photodetectors to mark and ascertain the position of the carriage 108. An interrupter flag 141 (FIG. 12) is secured by screw 142 and washer 143 to probe mount 144. Photodetectors 145–147 are secured to circuit board 148 which is in turn secured to the motor mount plate 95 by brackets 149 and 150. The end portion of interrupter flag 141 extends downwardly into the photodetector 145 when the probe tube is in the wash cup, or in other words when carriage 108 is in the position shown in FIG. 20C. Similarly, the interrupter flag extends into photodetector 146 when the carriage is in the position of FIG. 20E and the probe tube is in the sample cup. Interrupter flag 141 extends into photodetector 147 when the carriage is in the position of FIG. 20A and the probe tube is in the standard cup.

Figure 13:
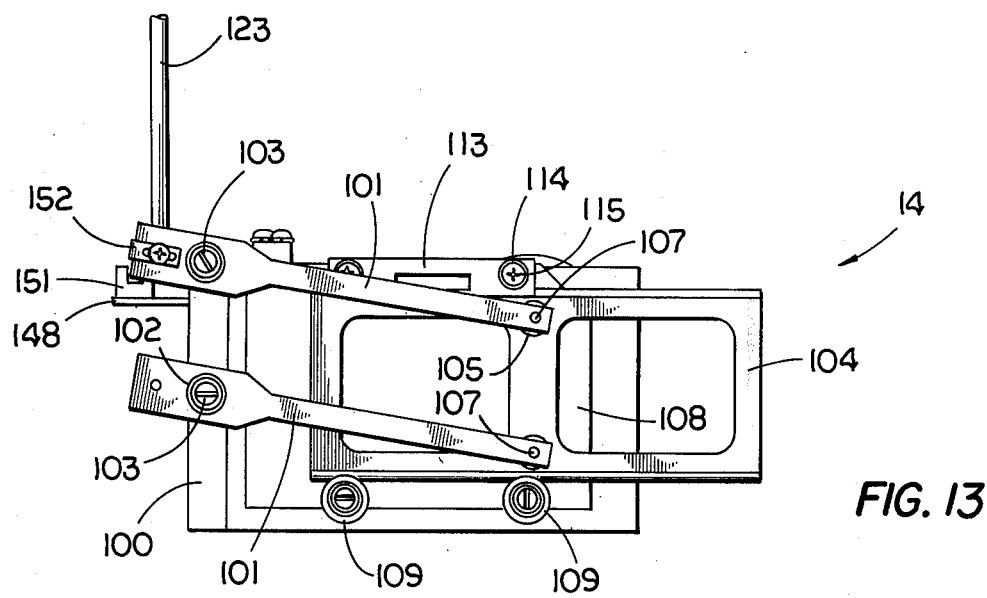
FIG. 13 is a partial, side elevational view of the sampling probe mechanism of FIG. 12.
Figure 14:
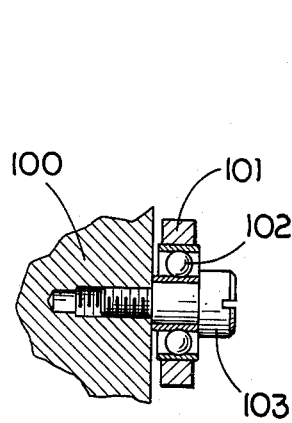
FIG. 14 is a partial end cross-sectional view showing the mounting of the arms of the sampling probe mechanism secured to the probe mount block.

An additional photodetector 151 is mounted to the circuit board 148 and a corresponding interrupter flag 152 (FIG. 13) is secured to the back end of the upper arm 101. As shown in FIG. 13, the interrupter flag 152 is withdrawn from the photodetector 151 when the carriage is in the lowered position, corresponding to any of the carriage positions shown in FIG. 20A, 20C or 20E. When the carriage is lifted in the intermediate air draw positions such as shown in FIGS. 20B and 20D, the arms 101 are pivoted upwardly and the interrupter flag 152 is received within photodetector 151.

In this manner, the photodetectors 145–147 and 151 provide information defining the position of the carriage and therefore of the probe tube. This information may be utilized in various respects, and particularly to assure the proper times for indexing the carousel. For example, it is apparent that the carousel should not be permitted to rotate when the sample probe is in either a standard cup or a sample cup, and this is indicated by the presence of the interrupter flag 141 in either of photodetectors 146 or 147, and by the absence of interrupter flag 152 from photodetector 151.

The sampling transfer probe together with the sample carousel and wash cup provide a means for introducing standard or test sample; wash and air segments into the analyzer. As previously indicated, standards or samples are contained in sample cups carried by the carousel. A wash solution is continuously pumped through the wash cup. In addition, reagent solutions are typically provided which are pumped into the flow streams within the analyzer and are combined with the sample segments to effect the desired reactions. These reagents are maintained in a refrigerator unit preferably forming a portion of the analyzer.

Figure 21:
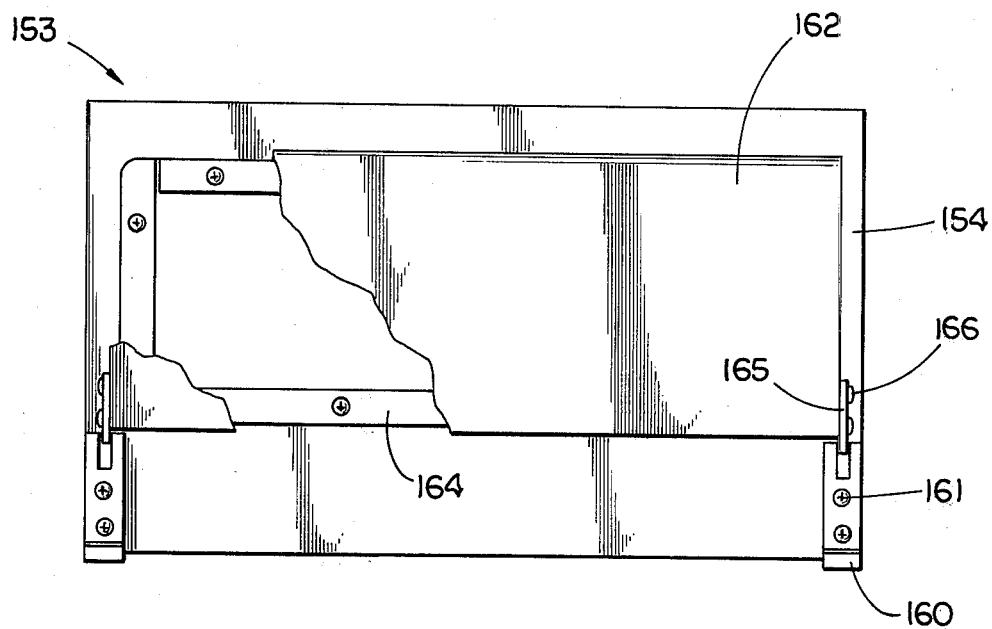
FIG. 21 is a front elevational view of a refrigerator unit useful in the present invention.
Figure 22:
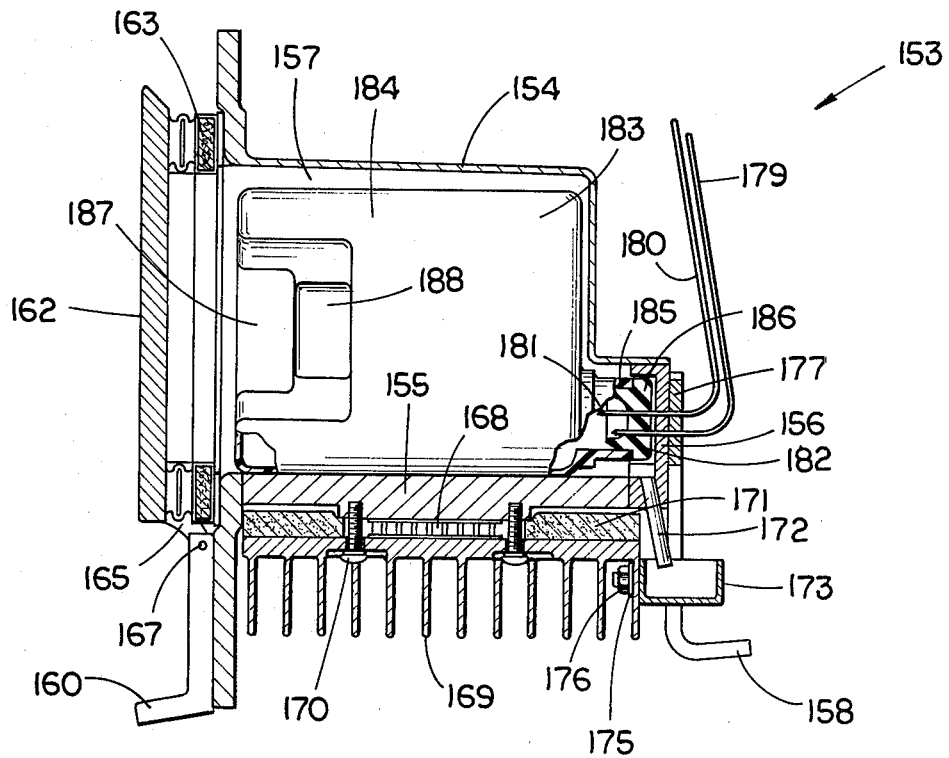
FIG. 22 is a side, cross-sectional view of the refrigerator unit of FIG. 21.
Figure 23:
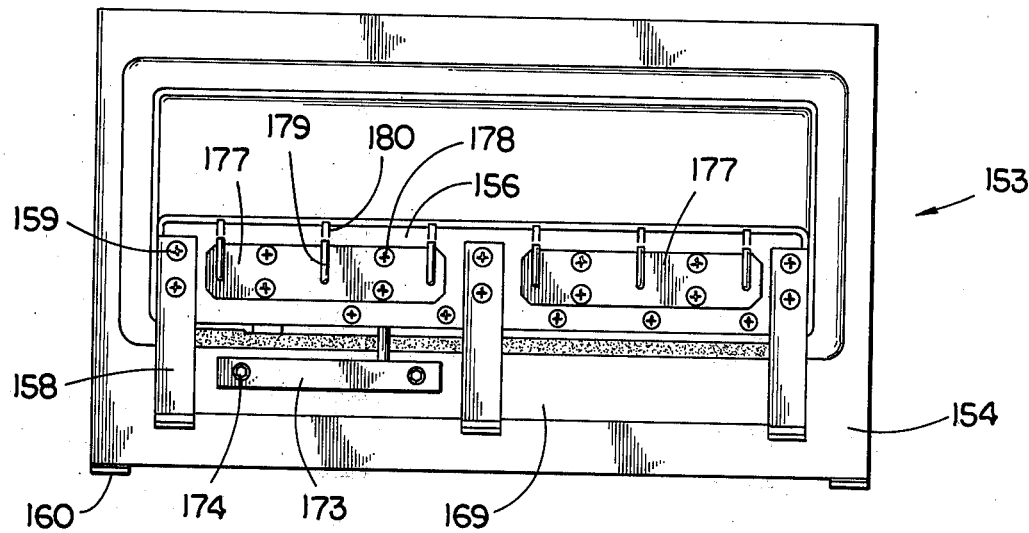
FIG. 23 is a rear, elevational view of the refrigerator unit of FIG. 21.
Figure 24:
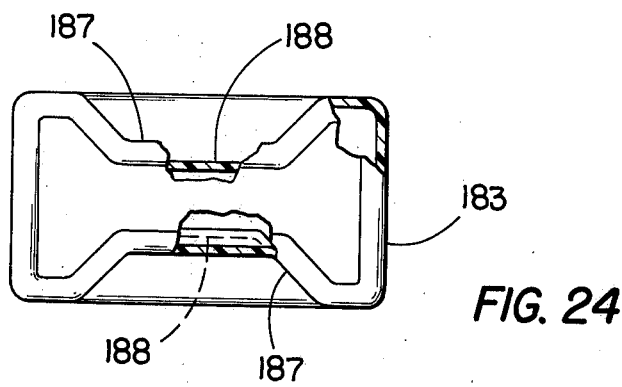
FIG. 24 is a bottom, plan view of a refrigerator bottle useful in the present invention.

A preferred embodiment of a refrigerator unit useful with the present apparatus is shown in detail in FIGS. 21–23. FIG. 21 is a front, elevational view of the refrigerator unit 153. FIG. 22 is a side, cross-sectional view and FIG. 23 is a rear elevational view of the refrigerator unit. Refrigerator unit 153 includes a housing 154 having secured thereto a floor block 155 and a wall block 156 to define a refrigerator chamber 157. Rear legs 158 are secured to the wall block 156 with screws 159. Front legs 160, which serve also as hinge brackets for the door, are secured to the housing 154 with screws 161. Refrigerator door 162 is mounted to the refrigerator housing and includes insulated perimetric seals 163 (FIG. 22) which are positioned to engage inserts 164 bordering the refrigerator chamber. Hinges 165 are secured to the sides of door 162 by screws 166, and are hingedly mounted to the front legs/hinge brackets 160 by pins 167. Thus, the refrigerator door 162 is mounted for a conventional, hinged opening to provide access to the refrigerator chamber.

A peltier module 168 and heat sink block 169 are mounted to the floor block 155 by screws 170 (FIG. 22). In conventional fashion, the peltier module is employed in conjunction with the heat sink block to provide the reduced temperatures within the refrigerator chamber. The refrigerator chamber is preferably maintained at 5° C.±3° C. Insulation 171 is provided between the heat sink block 169 and the floor block 155 to further assure appropriate temperature control within the refrigerator chamber. A drain tube 172 is secured within wall block 156, and communicates with the refrigerator chamber 157 to provide a drain for materials therein. Drain tube 172 is directed externally to evaporation pan 173 which is secured to the heat sink block 169 with bolts 174, washers 175 and nuts 176.

A pair of tube blocks 177 is mounted to the wall block 156 with screws 178. The refrigerator chamber 157 is sized to receive several fluid containers, typically six containers. A pair of tubes is provided at each location for such containers. For each container there is provided a first, lower tube 179 and a second, upper tube 180. Each of these tubes is received within suitable, aligned apertures in the tube block 177 and wall block 156. The ends of the tubes received within the refrigerator chamber are provided with piercing points, such as 181 (FIG. 22), for insertion through a septum 182 provided as a cover for the refrigerator bottles 183. Preferably, the septum 182 comprises a stopper of a rubber or similar material which is received within an opening in the bottle 183. The stopper is frictionally fit within the opening and is sealed to the bottle with an adhesive material. A third tube (not shown) may also be provided as a sensing mechanism to assess the fluid level in the refrigerator bottles. Preferably, the microprocessor is provided notice when a particular full bottle is placed in the refrigerator and thereafter monitors usage of the bottle contents and signals when the fluid is nearly depleted. For example, in a typical embodiment the microprocessor is programmed for 500 tests for a given bottle, and an alarm is sounded when a given number of tests have been conducted since insertion of each bottle.

The described refrigerator unit is preferable in several respects. The unit is simple in construction and facilitates accurate and even control of the temperature in the refrigerator chamber to assure proper maintenance of the liquids maintained therein. The refrigerator provides for drainage and collection of spilled or leaked liquids, and is conveniently designed and located for accessibility. The bottled reagents and other liquids are quickly and easily replaced and the liquid levels may be monitored to signal needed replacement.

A preferred form of the bottles used in conjunction with the refrigerator unit is shown in FIGS. 22 and 23. The bottle may be formed from a variety of materials, and suitably is molded from a high density polyethylene. Bottle 183 includes a body portion 184 and a neck portion 185. The stopper 186 including the septum portion 182 is received within the neck portion of the bottle and includes a lip which rests adjacent the top of the neck portion. Recesses 187 are provided at the bottom of bottle 183 to provide reinforcement for the bottle at that location and to provide a means for gripping the bottle for insertion into and removal from the refrigerator. Further recesses 188 are provided and serve to further reinforce the bottom portion of the bottle for insertion into and removal from the refrigerator chamber. In addition, the recesses 188 facilitate grasping of the bottle by providing a shoulder between the recesses 187 and 188 to assist grasping of the bottle.

The reinforcement of the bottles is desirable particularly at the times of insertion into and removal from the refrigerator chamber. At these times, the tubes 179 and 178 are being inserted into or removed from the septum of the bottle stopper 186. With the bottle being grasped at the reinforced recesses, the grasping of the bottle does not cause the fluid to be driven from the bottle into the tubes. In addition, the rectangular bottle design provides for a compact arrangement of the bottles within the refrigerator chamber, and the recesses provide a means for grasping the bottles while in this compact arrangement.

Figure 25:
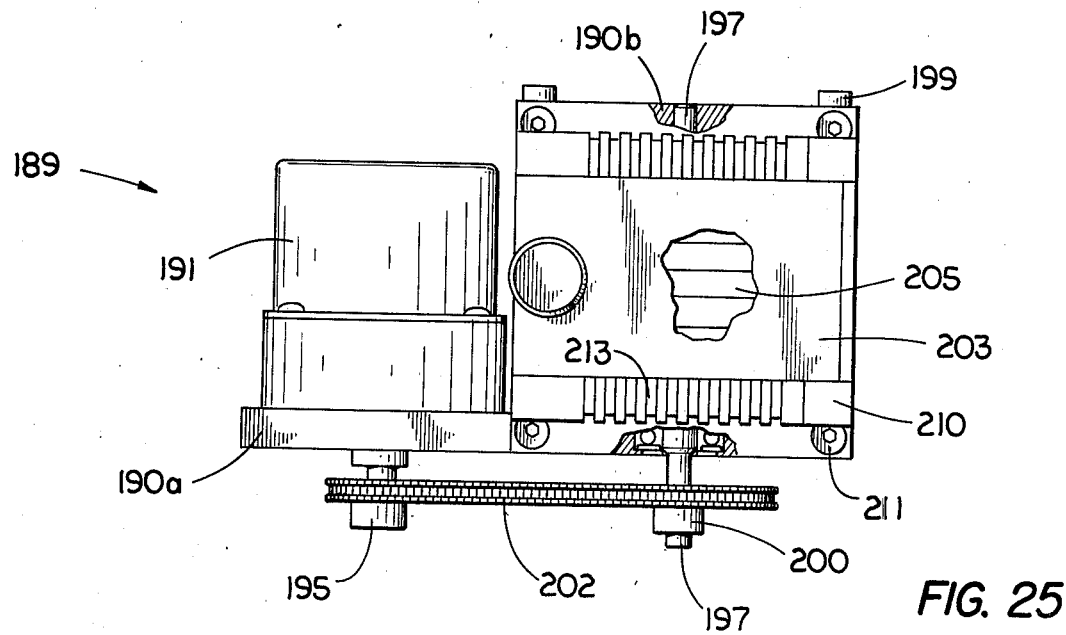
FIG. 25 is a top, plan view of a peristaltic pump useful in the present invention.
Figure 26:
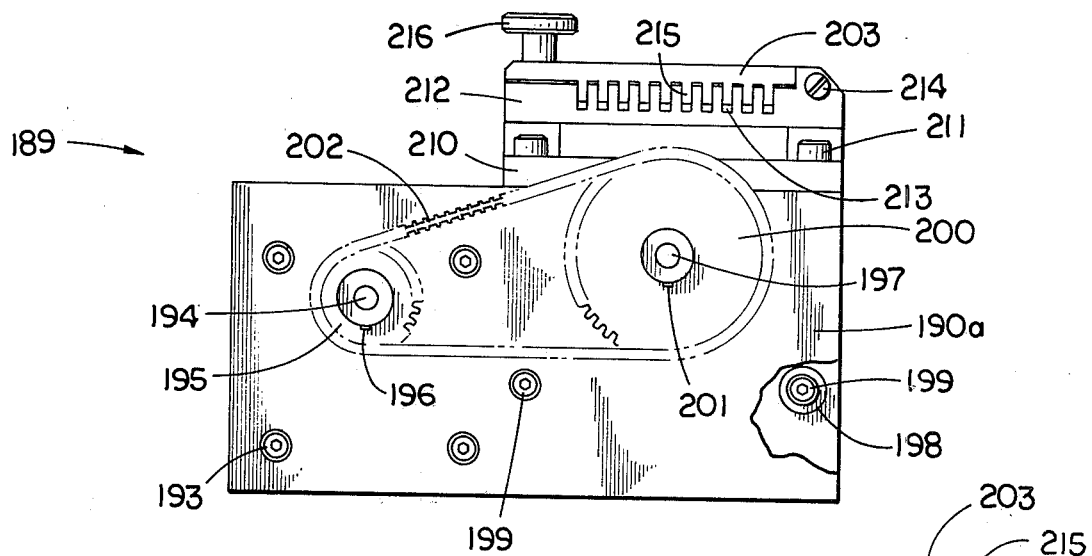
FIG. 26 is a side, elevational view of the peristaltic pump of FIG. 25.
Figure 27:
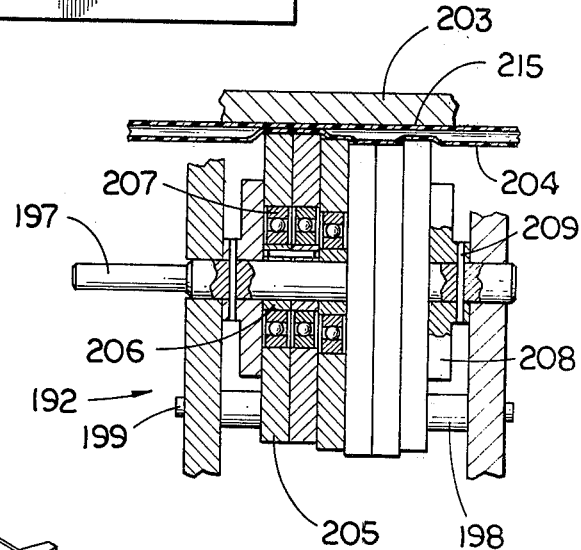
FIG. 27 is an end, partially cross-sectional view of the cam shaft assembly of the peristaltic pump of FIG. 25.

The system fluids, including the samples, standards, diluents, wash and air segments, are preferably drawn into and moved through the continuous flow portion of the analyzer by a suitable continuous flow pump means, which most preferably comprises a peristaltic pump assembly. FIG. 25 shows a top, plan view of a preferred embodiment of a peristaltic pump assembly 189 useful in the present analyzer. FIG. 26 is a side, elevational view of the pump assembly 189, and FIG. 27 is an end, partial cross-sectional view of the cam shaft assembly utilized in the pump assembly of FIG. 25. Peristaltic pumps may provide a somewhat intermittent flow, but the flow is substantially continuous and is intended to be encompassed by the term continuous flow as used herein and generally in this art. Peristaltic pumps are useful because of their simple, reliable and durable construction. Such pumps, and particularly the peristaltic pump described herein, provide a constant and consistent fluid flow through the system and are readily adapted for use with various numbers of pump lines.

The pump assembly 189 comprises opposed mounting plates 190a and 190b to which the pump motor 191, such as an A. W. Haydon model no. K86118-44 motor, and cam shaft assembly 192 (FIG. 27) are mounted. The pump motor is mounted to mounting plate 190a with screws 193 and includes a drive shaft 194 extending through the mounting plate. A motor gear 195 is secured to the drive shaft 194 by set screw 196. Opposed ends of the cam shaft 197 are received in apertures defined by the mounting plates 190a and 190b. The cam shaft and associated cams are held between the mounting plates by the securement together of the mounting plates with plate spacers 198 and screws 199. A cam shaft gear 200 is secured to the cam shaft 197 by means of a set screw 201. A drive chain belt 202 extends around and drivingly connects the cam shaft gear 200 and the motor gear 195.

As is customary for peristaltic pumps, the pump motor drives a cam shaft assembly which cooperates with a pressure plate 203 to drive fluid through the tubes received between the cams and the pressure plate. The pump rates and relative flow stream proportions are readily controlled by selection of tubes with various desired internal diameters. As shown in FIG. 27, the tubes 204 are received between the cam-driven pump links 205 and the pressure plate 203. For each pump link, there is a cam 206 secured to the cam shaft and received within a radial bearing 207. Each bearing 207 is received within a cam link 205. The several cams are oriented with respect to the cam shaft such that rotation of the shaft will cause successive ones of the pump links to move toward the pressure plate 203. In this manner, the tubes 204 are occluded first at the upstream pump link and then successively through the following pump links to draw fluid into the pump and force the fluid ahead of the occlusion and into the remainder of the system. Received on opposite sides of the pump links are thrust washers 208 secured to the cam shaft with roll pins 209 which are received within aligned apertures in the thrust washers and the cam shaft.

The mounting plates 190a and 190b are secured to the pump body 210 (FIG. 26) by screws 211. Pump body 210 includes a grid plate 212 which defines several parallel channels 213 within which the tubes 204 are received. Pressure plate 203 is hingedly mounted to the pump body with screws 214, and the pressure plate includes ridges 215 which are received within the channels 213 upon closing of the pressure plate. The pump links cooperate with these ridges to occlude the tubes in the manner previously described to force fluid through the tubes into the system. In one embodiment, a thumb screw 216 is mounted to the pressure plate 203 and is used in customary fashion to secure the pressure plate to the pump body 210 in the closed position. Release of the thumb screw permits the pressure plate to be pivoted upwardly for access to the channels 213 and the tubes received therein. A latch mechanism or other securement means may similarly be provided for securing the pressure plate in the closed position for operation of the peristaltic pump.

Figure 28:
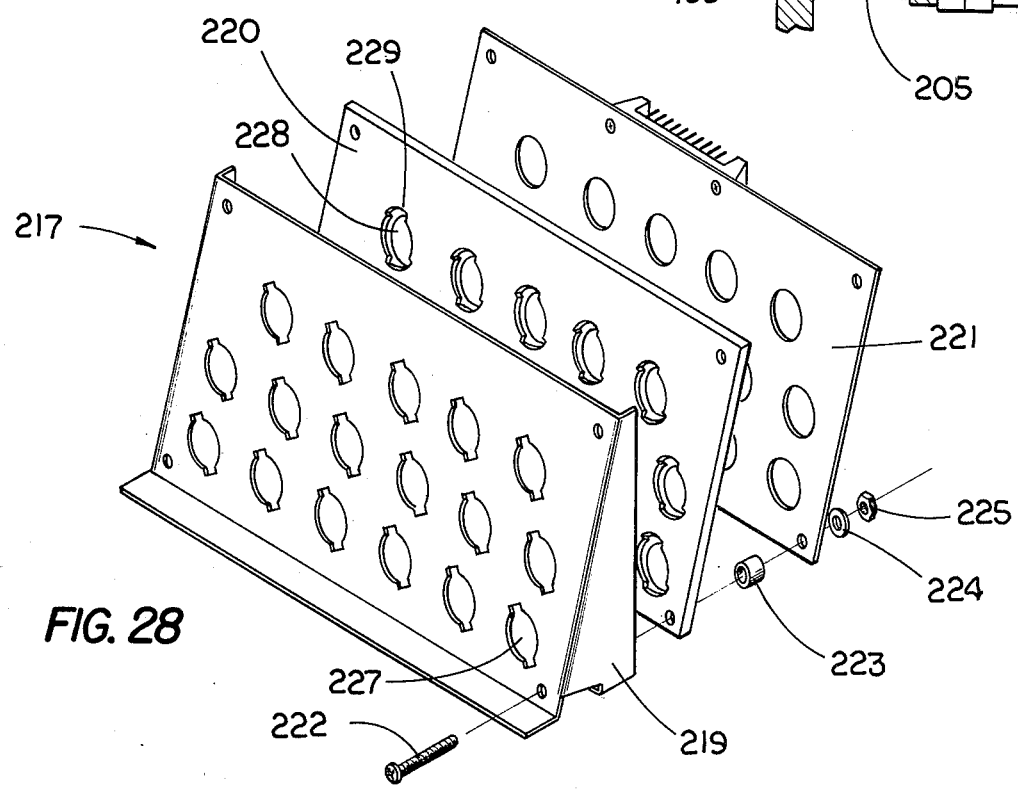
FIG. 28 is a perspective, exploded view of a valve assembly useful in the present invention.
Figure 29:
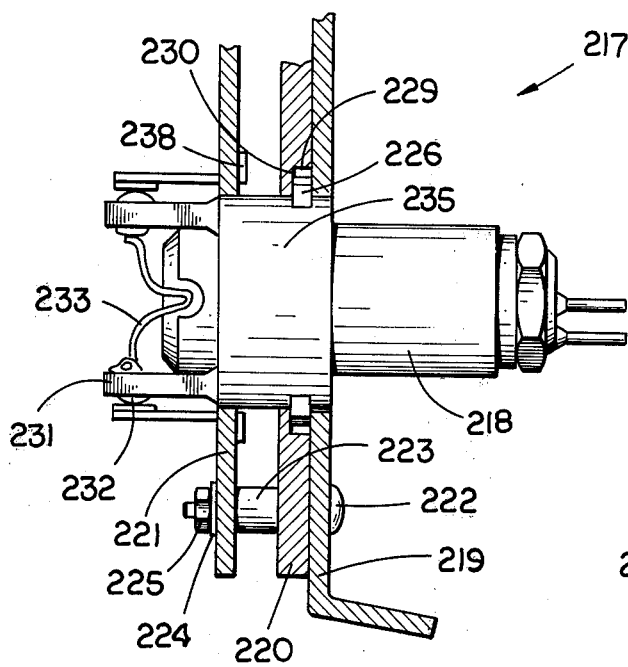
FIG. 29 is a side, partially cross-sectional view of a portion of the valve assembly of FIG. 28, and particularly showing the mounting of a valve in the assembly.
Figure 30:
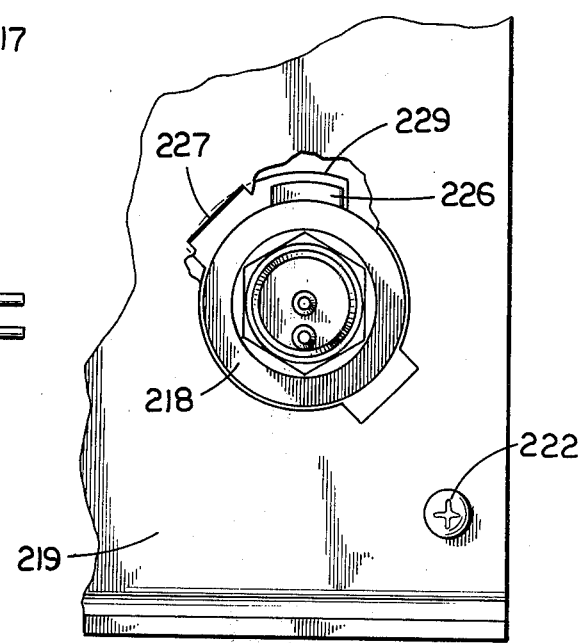
FIG. 30 is a front view of the valve and assembly of FIG. 29.

The analyzer further preferably includes a valve means for interconnecting the several apparatus components and for enabling control of fluid flow into the system and among the various components. The valve means most preferably comprises a valve assembly 217 supporting several cartridge valves 218 (FIG. 29). The valve assembly includes a valve holder assembly comprising a face plate 219, subpanel 220 and valve board 221 secured together by screws 222, spacers 223, washers 224 and nuts 225. The valves 218 are provided with opposed flanges 226 utilized for mounting the valves to the valve holder assembly. For each valve to be mounted there is provided in the face plate 219 an aperture 227 (FIG. 28) having a generally circular shape but including opposed notches corresponding to the flanges 226 provided on the valves. The subpanel 220 is also provided with a generally circular aperture 228 for each valve mounting location. However, the apertures 228 in the subpanel 220 include oversized, opposed notches 229 which extend less than the full depth of the subpanel. This may be readily accomplished, for example, by forming the subpanel of two separate panels having the appropriate cut-outs. In this manner, the valves may be mounted by inserting the body of each valve through the circular portion of the associated apertures 227 and 228 in the face plate 219 and subpanel 220, respectively, and inserting the flanges 226 through the opposed notches in the face plate aperture 227. Having passed the flanges past the face plate, the oversized notches 229 in the subpanel aperture permit the valve to be rotated to move the flanges 226 out of alignment with the notches in the face plate aperture. Since the notches 229 are provided for less than the full depth of the subpanel, the flanges are held between the face plate and the portions 230 of the subpanel located below the notches. This manner of mounting the valves 218 is particularly advantageous since the valves are readily inserted and removed for replacement purposes. The valves in the analyzer receive continuous use during operation of the analyzer, and the provision of a quick and simple means for replacing worn out or defective valves is highly desirable.

Figure 31:
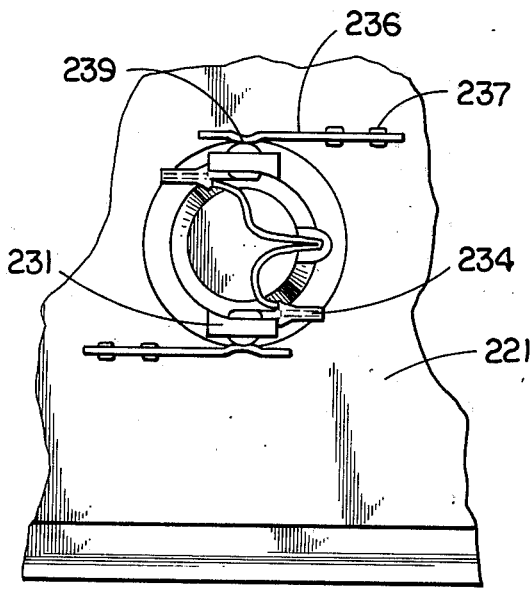
FIG. 31 is a rear, elevational view of the valve and assembly of FIG. 29.

The electrical connections for the valves 218 are provided with the valve board 221 as shown particularly in FIGS. 29 and 31. The valves 218 are provided with legs 231 secured to which are contact rivets 232. Typically, the legs 231 comprise portions of a jacket 235 secured, such as by gluing, to the cylindrical body of a solenoid valve. In this manner, presently available solenoid valves, such as the Angar valves, no. 336010, useful herein, may be readily converted to use in the manner described by fitting the jacket 235 to the valve body and connecting the valve wires to rivets or other contact means provided in the jacket. The wires 233 of the valve are electrically coupled with the contact rivets 232, the connection preferably being covered with a heat shrinkable sleeving 234 (FIG. 31).

Contact elements 236 (FIG. 31) are mounted to the valve board and positioned to contact the rivets 232 upon insertion of a valve 218. Apertures 237 are provided in the valve board and receive prongs 238 (FIG. 29) extending from the contact members 236. The prongs extend through the apertures in the valve board and are secured to the opposite side of the valve board to hold the contact members in place adjacent the valve contact rivets. The curved portions 239 of the contact members are provided such that rotation of the valves upon mounting in the valve holder assembly will resiliently urge the contact members slightly outward to assure a good contact with the rivets.

Figure 3:
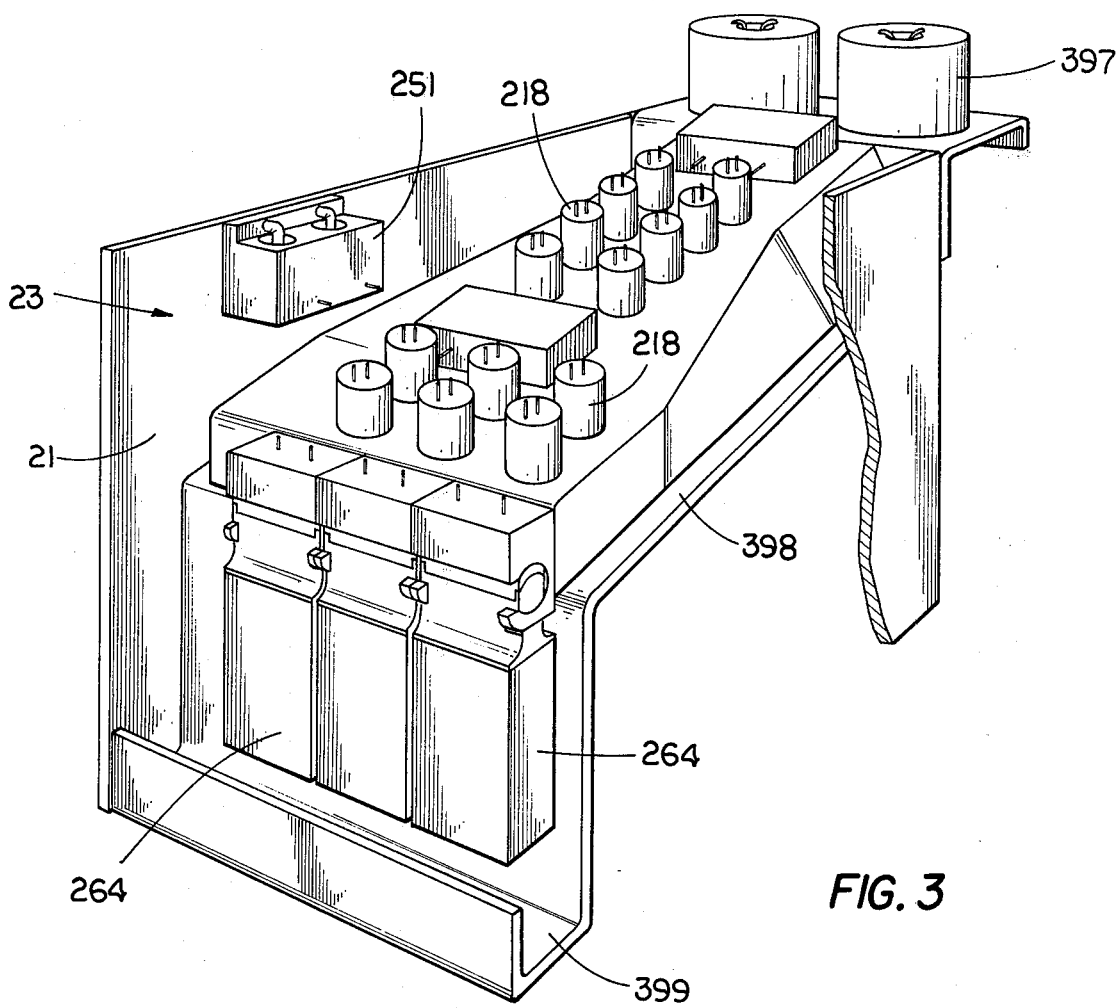
FIG. 3 is a front perspective view of the discrete flow portion of the apparatus of FIG. 1.

The valve assembly 217 accommodates the several valves utilized to control fluid flow in the continuous flow portion of the present apparatus. The several valves and other components of the apparatus are interconnected as later described with respect to FIG. 45 and operate under microprocessor control. A similarly constructed valve assembly is preferably included in the discrete flow portion as shown in FIG. 3. The interconnections of the valves and components associated with the discrete flow portion of the present apparatus are also described in conjunction with FIG. 45.

Figure 32:
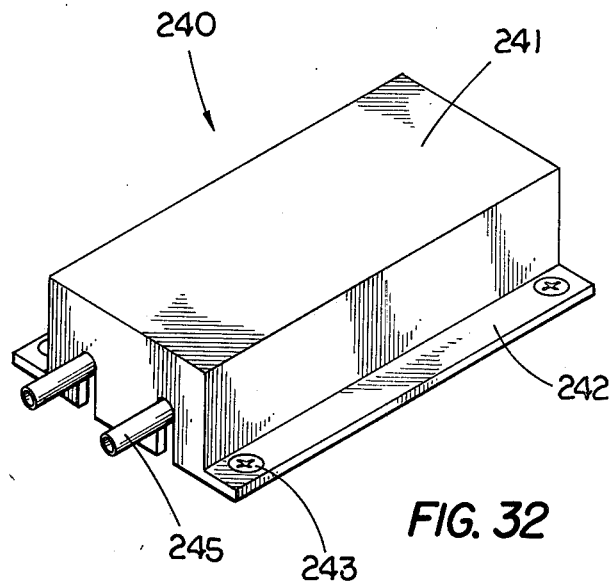
FIG. 32 is a perspective view of an incubator assembly useful in accordance with the present invention.

The system fluids, preferably in the continuous flow portion of the analyzer, are moved through an incubator means for providing a uniform temperature for the fluids. A preferred embodiment of an incubator assembly 240 useful in the present apparatus is shown in FIGS. 32 and 33. Incubator assembly 240 includes an incubator housing 241 which is generally rectangular and includes a pair of flanges 242 secured to the analyzer chassis 11 by screws 243. Fluid coils 244 are contained within the incubator housing and include ends, such as 245, which extend from the housing for connection with the analyzer tubes. The fluid coils 244 are mounted within rectangular housings 246 formed of a heat conductive material, preferably a metal such as aluminum. The coils are suspended in a filler material 247 contained in the housings 246, the filler being heat conductive and preferably comprising an epoxy material containing, for example, aluminum filings to provide heat transfer. A film, resistive heating element 248 is mounted at the top and bottom of the rectangular housings 246, and thermistors 249 are located adjacent each of the heating elements at about their center. The housings 246 are mounted to the incubator housing 241, and insulation 250 is received between the housings 246 and incubator housing 241. The incubator is typically operated to maintain a temperature at the coils of about 40° C.±1° C. The described incubator is simple in construction and provides an even temperature to the fluid coils, which temperature is simply and accurately monitored controlled.

The system fluids in the continuous flow portion of the analyzer move in a continuous manner until reaching collection means for separately collecting the sample segments and the intersample segments. The collection means preferably include collection cups shown in a preferred embodiment in FIGS. 34-36. The collection cups 251 comprise a body portion 252 defining a pair of generally cylindrical cavities or cups 253 each of which has a conical bottom 254. Apertures 255 and 256 extend inwardly from the front wall 257 and rear wall 258, respectively, and communicate with the interior of the cups 253 at about the center of the conical bottoms. Tubes 259 and 260 are received within the apertures 255 and 256, respectively, and provide fluid communication between the collection cups and the subsequent components of the analyzer apparatus.

The collection cups are mounted to the analyzer chassis, preferably wall 21 (FIGS. 3 and 36), by screws 261 received in apertures in the rear wall 258. The body portion 252 of the collection cups includes a flange 262 extending about the front and side walls. A cover 263 may be positioned over the collection cups and received against the flange 262. Use of the cover is particularly preferred in handling radioactive materials, and is generally preferable to avoid the possibility of contamination to or from the sample segments.

The collection cups alternately collect the sample and intersample segments. In the preferred RIA embodiment of the present apparatus the sample segments gathered in the collection cups are passed to a separation means, and the liquid portion of the intersample segments are moved to a waste collection means, typically through different ones of the apertures 256 and 257. The separation means for the RIA embodiment of the present apparatus provides a means for separating the components of the reaction mixture to enable counting of the appropriate, test components. Typically the bound components are separated from the unbound components and the test components to be counted, typically the bound components, are passed into the flow cell.

In the RIA embodiment, the preferred separation means comprises a resin column means for selectively binding either the bound or unbound components to a resin or other material or structure. For example, preferred resins for the RIA embodiment include polystyrene resins nos. A6-21K and AG1X4 of Bio Rad Laboratories, Richmond, Calif. 94804 for the T4 and T3U uptake tests, respectively, and resin no. LS-90 of Lab Systems, Inc., San Mateo, Calif. 94401 for the digoxin tests. Alternatively, other separation means for RIA tests are known and are useful with the present apparatus. It will be appreciated that for non-RIA embodiments of the present apparatus, the separation means may comprise other types, such as filtration or centrifugation, and these are well known in the art. In such uses, it may be preferable to include the separation means in the continuous flow portion of the apparatus, particularly if a slower flow rate, such as is employed in the continuous flow portion, is preferable to effect separation. It will also be appreciated that in certain embodiments of the present apparatus the separation means will not be necessary or useful. For example, colorimeter tests or reaction products will not utilize a separation of the reaction products.

The preferred resin column means comprises a resin column arrangement as shown in FIGS. 34-41. The resin column is conveniently provided as a cassette 264 comprising a column block 265 and a cover 266 mounted thereto. Cap 267 is secured to the top of column block 265 and includes upraised o-ring portions 268, which may include separate o-rings, encompassing a pair of apertures 269 extending through the cap. Column block 265 additionally defines passageways 270 and 271 aligned and communicating with the apertures 269. Passageway 270 expands to a generally cylindrical bore within which is secured a filter 272 and column 273. Column cap 274 defines a generally cylindrical bore within which is secured a filter 275 and the opposite end of the column 273. Column cap 274 defines passageways 276 communicating with the interior of the column. Tubing 277 connects at one end with the passageway 271 and at the other end with the passageways 276 in the column cap, thus providing communication between the respective passageways. A suitable resin or other separation material 278 is contained within column 273.

A complementary receptacle 279 (FIGS. 40 and 41) provides a simple and quick hook-up for the cassette 264. Receptacle 279 includes a pair of C-shaped arms 280. Resin column cassette 264 includes projections 281 and slots 282 for cooperation with the C-shaped arms 280 to provide a firm connection of the cassette and the receptacle. For installation, the casette is inserted into the C-shaped arms in a position perpendicular to the receptacle, and is then rotated 90° to be parallel with the receptacle as shown in FIG. 41. The C-shaped arms 280 are received within the slots 282 and bear against the projections 281 to hold the cassette in position against the receptacle. The receptacle defines a pair of passageways 283 which are positioned to align with the apertures 269 in the cassette cap, as shown in FIG. 41, to provide fluid communication with the resin column. Additional details of the resin column cassette and receptacle, particularly pertaining to the method and manner of attachment, are included in United States patent application, Ser. No. 16,429, for a "Sealing Connector for Liquid and Gas Systems" filed by David C. Fudge on Mar. 1, 1979, and incorporated herein by reference.

The sample segment fluid is separated into waste and test components as it is passed through the separation means. The test components are then moved to an analysis means, which in the RIA embodiment preferably comprises a flow cell received in a gamma counter. A preferred embodiment for a flow cell useful in the present apparatus is shown in FIG. 42. The flow cell simply comprises a coil of tubing 420 having an inlet 284 and an outlet 285. The tubing coil is contained within a cylinder 286 preferably formed from an epoxy or other suitable material. A preferred flow cell comprises a molded acrylic cylinder, ½ inch high and ⅝ inches in diameter, with a coiled teflon tube having an internal volume of 0.65 cc. The flow cells in the preferred RIA embodiment of the present apparatus are positioned within suitable gamma counters 397 (FIG. 3) in known fashion to provide for measuring the gamma radiation which in the RIA embodiment evidences the sample properties desired to be known. A typical gamma scintillation detector comprises a high voltage (800 v) photomultiplier tube with a 1 and ¼ inch diameter thallium activated NaI scintillation crystal mounted as a common assembly with a protective aluminum skin. The NaI (sodium iodide) crystal includes a ⅝ inch well in which the flow cell is received. A separate counter is provided for each of the two flow channels.

For the non-RIA embodiments of the present apparatus, other various analysis means are employed as well known in the art. For example, other tests may perform analysis of the test components by colorimetry, UV or IR spectrophotometry, spectroflorometry, gas chromatography, mass spectroscopy, luminescence or other means.

Figure 43:
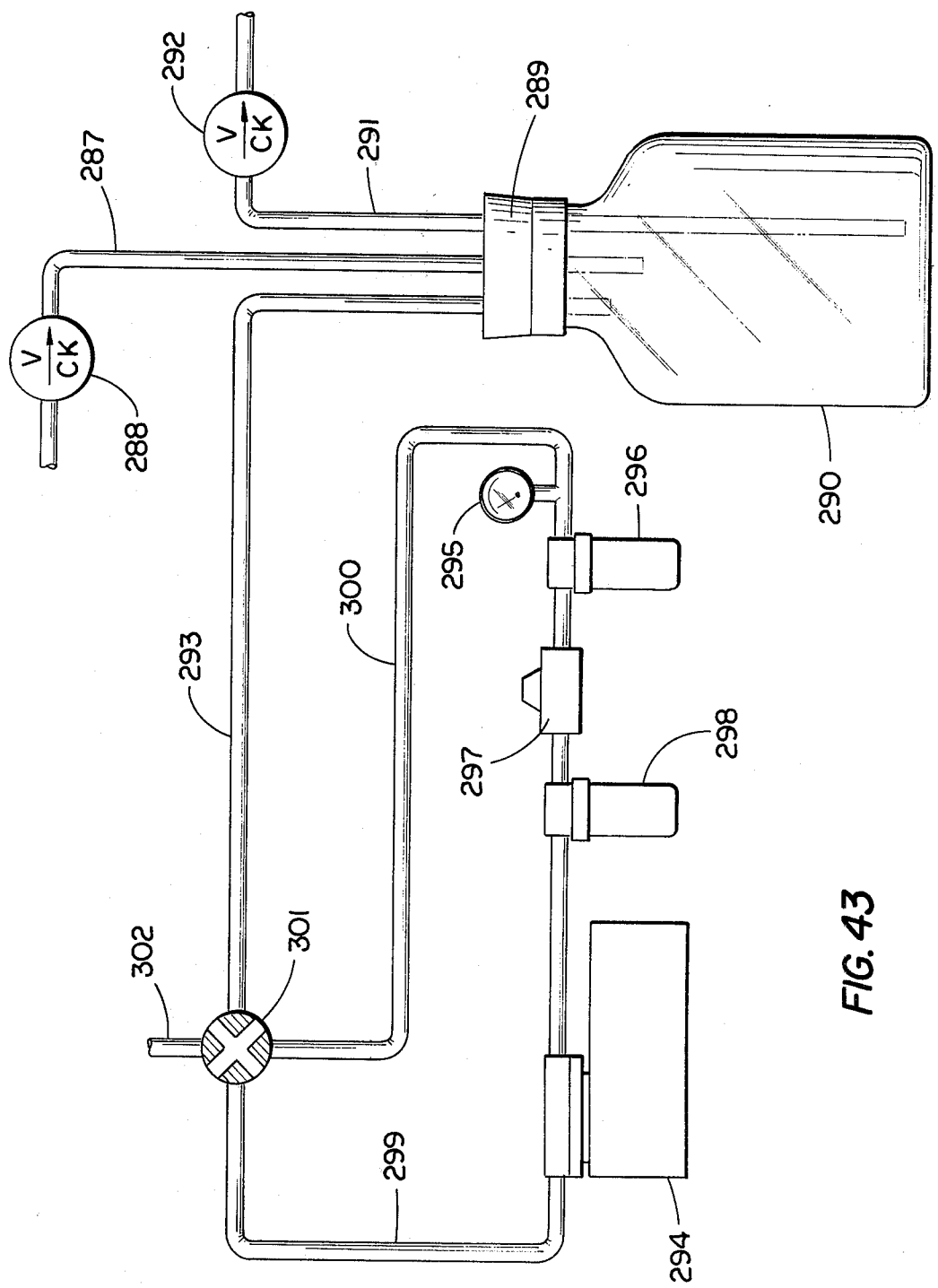
FIG. 43 is a partially schematic view of a waste collection system useful in the present invention.

The waste materials from the flow cells and other points in the system are removed to a waste collection means which preferably comprises a waste collection system as shown schematically in FIG. 43. The fluid waste is received through inlet line 287 which includes a check valve 288 to prevent backflow. Inlet line 287 communicates through a sealed stopper 289 with the interior of a retention bottle 290. Outlet line 291 similarly communicates with the interior of retention bottle 290 and includes a check valve 292 to prevent backflow from the waste container (not shown) to the retention bottle. A pressure line 293 is provided and communicates with the interior of the retention bottle to draw fluids into the retention bottle and to drive retained fluids to the waste container, as desired.

The analyzer includes a discrete flow means for moving the various fluid segments through the discrete flow portion of the analyzer. As used herein, the term discrete flow refers to the flow through the analyzer resulting from collection of the sample segments and periodically moving the collected sample segments to an analysis means. The discrete flow means also preferably operates to move the waste liquid to the waste collection means. Since the sample segments are collected prior to movement through the continuous flow portion, this movement may be quickly performed once the sample segment is collected. The sample segment may therefore be maintained in the analysis means for a longer period of time than if it were slowly introduced as by the continuous flow means.

The discrete flow means preferably utilizes a vacuum pump 294 to move the fluids in the discrete flow portion, and this pump is also preferably used in disposal of the waste fluids. As shown in FIG. 43, suitable apparatus are associated with the vacuum pump for normal operation, and these include pressure gauge 295, trap 296, regulator 297 and filter 298 arranged in series with the vacuum pump. Connected with the vacuum pump is a positive pressure line 299 and a vacuum line 300. A four way valve 301 is provided to selectively connect the positive pressure line and vacuum line of the pump with the pressure line 293 and the vent line 302.

In the normal operation, the positive pressure line 299 is connected to the vent 302, and the vacuum line 300 is connected with the pressure line 293 to draw a vacuum on the retention bottle and to thereby draw waste fluids into the bottle through line 287. This configuration is maintained for a predetermined amount of time to provide a collection of waste fluid in the retention bottle. After this time has elapsed, the four way valve 301 is switched to connect the positive pressure line 299 with the retention bottle pressure line 293, and to connect the vacuum line 300 with the vent line 302. In this configuration, the retention bottle is pressurized and the waste fluids contained therein are forced through the outlet line 291 to the waste container.

It will be noted that the check valves 288 and 292 are provided such that when a vacuum is drawn on the retention bottle, the waste fluids are permitted to flow through the inlet line 287 from the analyzer system, but are prevented from backflowing from the waste container to the retention bottle through outline 291. Similarly, the check valves 288 and 292 are disposed such that when the retention bottle is pressurized the check valve 288 prevents the waste fluid from flowing back into the system and also prevents the pressure from being applied to the system, while check valve 292 permits flow of the waste fluid through outlet line 291 to the waste container. The vacuum pump may typically operate at a 15 inch Hg vacuum pressure and a 3 psig positive pressure. The retention bottle preferably comprises a 2 liter glass bottle which is plastic coated for implosion/explosion protection.

In FIG. 44 there is shown a preferred embodiment for containing the diluent solution used by the analyzer and for collecting the waste fluids for disposal. A single unit 303 having a handle 304 contains a diluent container 305 and a waste container 306. These containers have threaded necks 307 and 308 which during storage are covered with caps 309 and 310, respectively. During use, the unit 303 is received within the liquid storage section of the analyzer and a diluent feed line 314 (FIG. 45) is connected with the diluent container and the waste outlet line 291 (FIG. 43) is connected with the waste container. The diluent and waste containers are preferably sized such that the waste container is sufficiently large to store all of the waste produced during use of the amount of diluent included in the diluent container. In this manner, the entire unit may be used in the analyzer until the diluent is exhausted, and at that time the associated waste fluid is collected in the waste container for disposal. The unit is then replaced with another unit having a diluent container charged with the desired amount of diluent and having an empty waste container.

Figure 45:
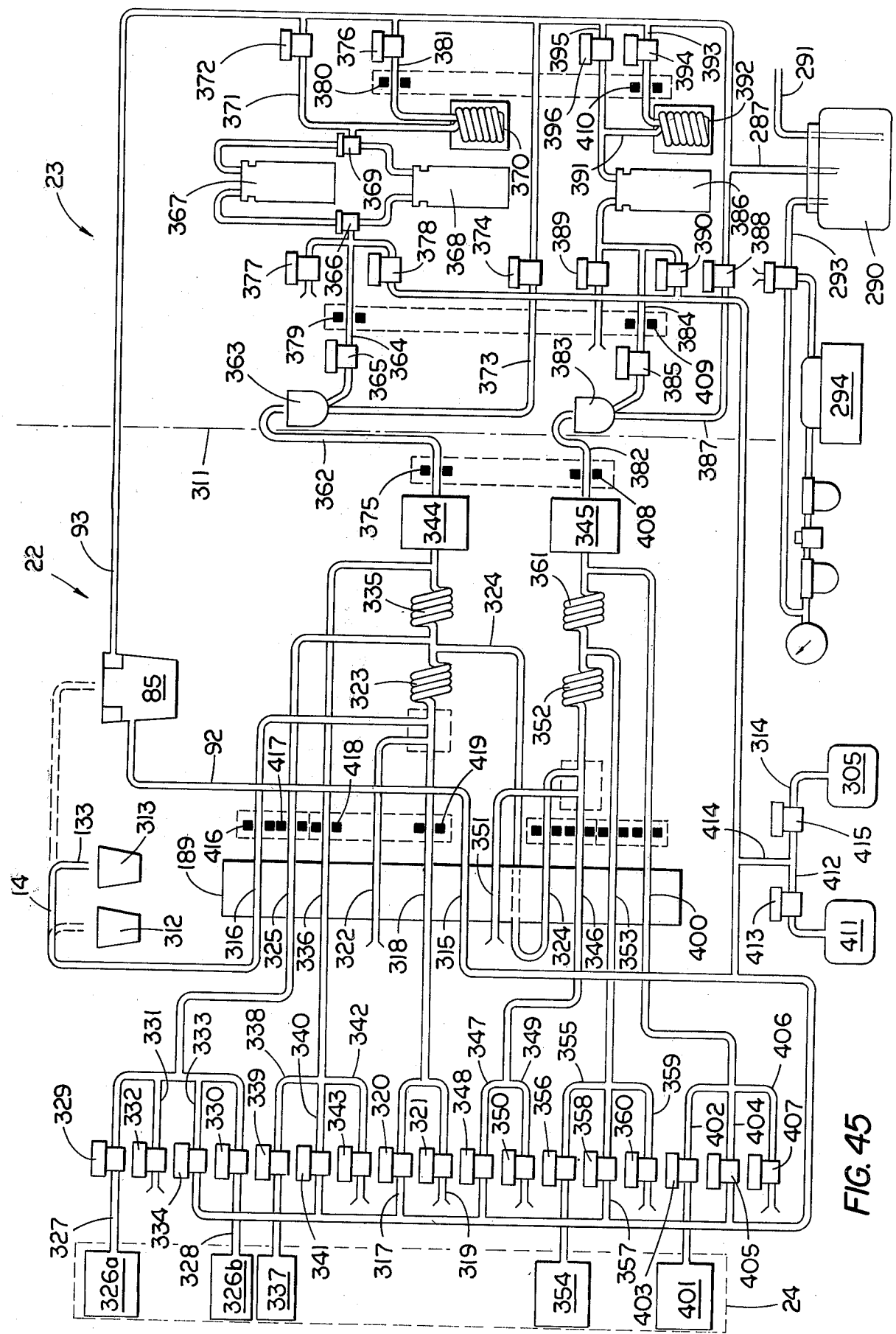
FIG. 45 is a flow diagram of a preferred embodiment of the chemical testing apparatus of the present invention.

A preferred embodiment of the present apparatus as a radioimmunoassay (RIA) analyzer is shown schematically in FIG. 45. Generally, the components to the left of line 311 comprise the continuous flow portion 22 of the analyzer and those components to the right of line 311 comprise the discrete flow portion 23 of the analyzer. As indicated, the driving force for the fluid segments in the continuous flow portion is preferably the peristaltic pump 189, and the driving force for the fluid in the discrete flow section is preferably the vacuum pump 294. The analyzer preferably is operable for use with T3U uptake, digoxin and $T_4$ procedures, and is therefore provided with two primary flow channels. Since the concentrations for the $T_4$ analysis are below that for the T3U uptake and digoxin procedures, a separate flow channel is utilized for the $T_4$ procedure. The difference in concentration requirements is accounted for by a resampling technique which will be described below.

The sampling probe mechanism 14 is operable to withdraw fluid segments from any of a standards sample cup 312 or an unknown sample cup 313 (carried on the sample carousel) or the wash cup 85. Diluent from the diluent container 305 passes through the valved diluent feed line 314 to the pump line 315 and eventually to the wash cup 85. The diluent is preferably used as the wash solution, although another liquid and container may be used if desired. Overflow of the diluent or other liquid in the wash cup 85 is removed through tube 93 to the retention bottle 290, by operation of the vacuum pump 294. The sample probe 14 is connected with the pump line 316 which operates to withdraw fluid samples from the appropriate sample, standard or wash cup. It will be appreciated that the peristaltic pump operates continuously to draw either a liquid or gas through pump line 316, which will depend upon whether the probe tube 133 is immersed in a fluid in one of the cups or is held in the air. This feature is utilized to provide fluid segments which are separated by air bubbles. The presence of the air bubbles, and of the fluid surfaces (and associated surface tensions) present on either side of the air bubbles, provides for cleaning the walls of the tubing between successive samples to prevent carry over.

Diluent from the diluent container 305 is drawn through diluent line 317 connected with primary (diluent) pump line 318. Air line 319 also connects with pump line 318. Diluent line 317 and air line 319 are provided with valves 320 and 321, respectively, to regulate the influx of diluent and air to the primary pump line 318. Typically, the valves 320 and 321 are alternated to provide a segmented flow of diluent samples divided by air segments in the primary pump line 318. Air pump line 322 is open to the air and joins primary pump line 318 downstream of the peristaltic pump. At this location, pump line 322 introduces additional air segments into the primary pump line 318. The air segments from the air pump line 322 are relatively smaller than the air segments already present in the primary pump line 318 due to the valving of air line 319.

The sample pump line 316 enters primary pump line 318 downstream of the air pump line 322. The segments then pass through a mixing coil 323, and a resample pump line 324 thereafter withdraws a portion of the fluid and air segments for the $T_4$ tests. Following the resample line, the desired tracer/buffer mixture is added to the primary pump line 318. It will be appreciated that the primary pump line 318 is useful alternately with the T3U uptake tests and the digoxin tests. For purposes herein, a detailed description will be provided only for the T3U uptake test arrangement, it being understood that similar description is appropriate, with reference to the respective components, for the digoxin tests. For example, pump line 325 is provided with alternating segments of tracer/buffer and diluent separated by air bubbles. Depending upon the tests to be run, the tracer/buffer may be either that for the T3U uptake test or for the digoxin test. The analyzer is provided with microprocessor control and corresponding control switches and inputs to operate the analyzer for various tests. Under this control, the various manipulations of the valves and other components are automatically performed to conduct selected tests.

The T3U uptake tracer/buffer container 326a and the digoxin tracer/buffer container 326b are maintained in the refrigerator 24 and feed lines 327 and 328, respectively, are connected therewith. Valves 329 and 330 are operated to supply a segment of the T3U uptake or digoxin tracer/buffer, respectively, to the pump line 325. Air line 331 is open to the air and is controlled by a valve 322 for providing intersegment air bubbles to the pump line 325. Diluent line 333 is connected to the diluent supply and is controlled by diluent valve 334 to supply diluent segments to the pump line 325 between successive segments of the tracer/buffer. The alternating segments of tracer/buffer and diluent, separated by air bubbles, within pump line 325 enter the primary pump line 318 downstream of the resample line 324 and immediately preceding a mixing coil 335.

Immediately downstream of the mixing coil 335 a pump line 336 joins the primary pump line 318. The fluid delivered through pump line 336 will depend upon whether a T3U test or a digoxin test is being conducted. In the case of a digoxin test, the pump line 336 will supply the digoxin antibody to primary pump line 318, whereas for the T3U test no antibody is used and instead of an antibody the diluent solution is provided to the primary pump line. The digoxin antibody container 337 is maintained in the refrigerator 24 and connects through digoxin antibody feed line 338, controlled by valve 339, to the pump line 336. Diluent line 340 having the diluent valve 341 also connects with pump line 336, as does air line 342 which is open to the air and has an air valve 343 associated therewith. For digoxin tests, the digoxin antibody valve 339, diluent valve 341 and air valve 343 are operated to provide alternating liquid segments of digoxin antibody and diluent separated by intersegment air bubbles. In the case of a T3U uptake test, only the diluent valve 341 and air valve 343 are used, and they are operated to provide successive diluent segments separated by air bubbles. These liquid and air segments move through pump line 336 and enter the primary pump line 318 downstream of the mixing coil 335 and upstream of the T3U/digoxin incubator 344.

Incubator means is provided, when required, to maintain the reaction mix in the sample segment at a uniform temperature to assure a reproducible reaction. Depending on the tests and therefore the reactions involved, the incubator means may have a variety of known constructions and operate under a variety of conditions and parameters. Further, for certain tests an incubator means will be unnecessary or of only limited need.

The incubator means preferably comprises an incubator constructed as shown in FIGS. 32 and 33, thus providing a tubing coil 244 through which the fluids pass. Further as shown in FIGS. 32 and 33, the T3U/digoxin incubator and the $T_4$ incubator 345 are preferably separate coils combined by providing a pair of such coils within a single incubator unit. The incubator coil provides a uniform temperature to the sample segments which comprise a reactant mixture, including for example the unknown sample, tracer/buffer and antibody (for digoxin), for a specific period of time. The coil shape is advantageous since it is symmetrical to provide uniform temperature control, is compact, and functions also as a mixing coil to assure proper distribution of the fluids for the reaction process.

A similar arrangement of components is provided for the other primary pump line 346. A diluent feed line 347 with associated valve 348 and an air line 349 with associated valve 350 connect with the primary pump line 346. Valves 348 and 350 are operated to provide successive diluent segments with relatively large intersegment air bubbles in a manner similar to that for the first primary pump line 318. Pump line 351 is open to the air and connects with the primary pump line 346 to provide numerous, relatively small air bubbles such as previously described with respect to air pump line 322. The resample pump line 324 connects with the primary pump line 346 downstream of the air pump line 351, and thus introduces into the primary pump line 346 a stream composed of liquid and air segments as previously described with respect to the primary pump line 318 at the location of the resample line. The segments then pass along primary pump line 346 through a mixing coil 352.

Downstream of the mixing coil 352 a pump line 353 connects with the primary pump line 346. Pump line 353 is comparable with pump line 325 in its operation, except that only a $T_4$ tracer/buffer is connected with the pump line 353. The $T_4$ tracer/buffer container 354 is maintained in the refrigerator unit 24 and connects through feed line 355 and associated valve 356 to the pump line 353. Diluent feed line 357 having associated valve 358 and air line 359 having associated valve 360 also connect with the pump line 353. Feed line valve 356, diluent valve 358 and air valve 360 are controlled to provide alternating segments of $T_4$ tracer/buffer and diluent, with intersegment air bubbles, to the pump line 353, and thereby to the primary pump line 346. Downstream of the connection between pump line 353 and primary pump line 346 there is provided a mixing coil 361.

Immediately downstream of the mixing coil 361 is the connection of pump line 400. The $T_4$ antibody container 401 is maintained in the refrigeraor unit 24 and connects through feed line 402 with associated antibody feed line valve 403 to pump line 400. Diluent line 404 with associated diluent valve 405 and air line 406 with associated air valve 407 also connect with pump line 400. The liquid and air segments in the second primary pump line 346 then pass through the $T_4$ incubator 345, which as previously indicated may conveniently be combined with the T3U/digoxin incubator 344 in a single unit.

A particular aspect of the present apparatus is the provision of automatic phasing of the initial sample, diluent, tracer/buffer and antibody segments in the continuous flow portion, and of the component operations in the discrete flow portion. As will be later described, the discrete flow portion includes photodetectors immediately downstream of the collection cups and flow cells. These photodetectors operate to detect the approach of sample segments to the collection cups to trigger evacuation of collected wash segments from the cups. They further detect the end of the sample segments presented to the collection cups, and thereby trigger evacuation of collected samples through the separation columns and into the flow cells. Additional photodetectors are included downstream of the flow cells to interrupt flow when the samples are in the flow cells for counting.

The continuous flow portion of the present apparatus includes several photodetectors for phasing the various liquid and air segments. Autophasing in the continuous flow portion of the analyzer is accomplished by detection of the relatively large bubbles immediately adjacent the sample segments and correspondingly located with respect to the diluent and reagent segments. Typically, these air segments have about a three second time length, as opposed to the other scrubbing air segments which have a time length of about one second and less. The photodetectors in the continuous flow portion are located immediately downstream of the peristaltic pump, and by appropriate microprocessor control are operable to detect only the three second air segments. The photodetectors may suitably be, for example, Optron OPB804 photodetectors comprising discrete photodiodes and detectors. The microprocessor is programmed to detect the presence of three second air segments as distinguished from the other, relatively smaller air segments. As before, the continuous flow portion preferably includes two primary flow paths, each of which are similarly controlled by the use of photodetectors. For this reason, a detailed description will only be given for the first of these flow paths, with comparable description being appropriate for the other flow path.

The photodetectors 416–419 are located along the sample/wash pump line 316, tracer/buffer pump line 325, antibody pump line 336 and primary pump line 318, respectively. The autophasing utilizes these photodetectors and the known times when the air valves 332, 343 and 321 admit the three second air segments into their respective lines to phase these air bubbles with the three second air bubble introduced into the sample line at the time the sample probe is moving between the sample or standard solution and the wash solution. When the sample probe moves from the wash solution to the standards sample cup 312 or unknown sample cup 313, one of the three second air segments is introduced into the sample pump line 316 immediately preceding the sample or standard segment. After the standard or sample is drawn from the respective cup, the transfer probe moves from the cup to the wash solution, introducing a three second air segment immediately following the standard or sample segment. These sample line air segments are detected when presented to the photodetector 416 and the three second air segments in the other pump lines are phased therewith.

Referring in particular to FIGS. 46A–46D, a detailed schematic of the liquid and air segments in the various pump lines of the first flow path is shown. Referring first to FIG. 46A, the sample pump line 316 is shown with its preferred segment flow. In FIG. 46A, there is shown a last portion of a wash segment $W_1$ at the juncture of the sample pump line 316 and primary pump line 318. The direction of flow in each of the pump lines is in the direction to the right in FIG. 46A. Immediately following the wash segment $W_1$ is a first three second air segment $A_3$ and then a sixty second sample segment $S_1$. Behind the sample segment $S_1$ is the following three second air segment $A_3$ and then alternating wash segments $W_2$ and air segments $A_1$ each of about one second duration. Thereafter follows the major wash segment $W_2$ followed by a three second air segment $A_3$.

As previously described, the three second air segments are introduced into the sample pump line 316 when the sample probe moves between the sample or standard cups and the wash cup. As depicted in FIG. 46A, a relatively large sample segment is withdrawn into the pump line and is bounded immediately preceding and following by three second air segments. Also as previously indicated, it is preferable that a plurality of wash segments be introduced between sample segments. These initial one second segments of wash and air are introduced by rapidly moving the sample probe into and out of the wash cup 85 prior to immersing the probe in the wash cup for a period of time to withdraw the remaining desired portion of wash segment. The probe is then moved back to a sample or standard cup, thus introducing a three second air segment immediately preceding a subsequent sample segment $S_2$. Thereafter a similar intersample segment, consisting of several alternating wash and air segments is introduced into the system preferably in a form as described between sample segments $S_1$ and $S_2$.

Further as shown in FIG. 46A, the primary pump line 318 includes three second air segments $A_3$ alternating with diluent segments. As shown, a portion of the diluent segment $D_{W1}$ is present at the juncture of sample pump line 316 and primary pump line 318, and is immediately followed by a three second air segments $A_3$. Following the air segment $A_3$ is a diluent segment $D_{S1}$ which is sized and timed, as will be further described, to correspond and join with the sample segment $S_1$. Air pump line 322 joins the primary pump line 318 and introduces several intrasegment air bubbles $A_S$ which perform primarily to assure mixing of components in the various segments as they are joined in the primary pump line 318. In addition, the intrasample air segments $A_S$ further operate as scrubbing bubbles within the diluent segments such as $D_{W1}$ which combine with the intersample wash segments such as $W_1$. Immediately following the diluent segment $D_{S1}$ is a three second air segment $A_3$ and a diluent segment $D_{W2}$. The latter diluent segment is sized and positioned to correspond and join with the wash segment $W_2$ at the juncture of the sample pump line 316 and primary pump line 318. Following the diluent segment $D_{W2}$ is a three second air segment $A_3$ and a diluent segment $D_{S2}$ which is sized and positioned to join with the sample segment $S_2$. The combined flow along primary pump line 318 passes through a mixing coil 323 to provide a good mixture of the diluent segments, such as $D_{S1}$, and the respective sample segments, such as $S_1$.

The result of the combination of the flow streams in sample pump line 316 and primary pump line 318 is shown in FIG. 46B. Starting at the juncture of the primary pump line 318 and tracer/buffer pump line 325, the primary pump line includes a combined wash and diluent segment $W_1D_{W1}$ divided into several portions by the intrasample air segments $A_s$. Thereafter there is included a three second air segment $A_3$ which is followed by the combined sample/diluent segment $S_1D_{S1}$. The sample/diluent segment is separated into several portions by the intrasample air segments $A_S$. Following the sample/diluent segment is a three second air segment $A_3$ and the combined wash/diluent segment $W_2D_{W2}$. At the front portion of the wash/diluent segment are the air segments $A_1$, which are followed by the relatively smaller intrasample segments $A_S$.

The resample pump line 324 withdraws a portion of the fluid moving through the primary pump line 318. Following the resample line is the juncture with the tracer/buffer pump line 325. Within the tracer/buffer pump line there is a segmented flow of alternating tracer/buffer segments such as $T_1$, and diluent segments D. As shown in FIG. 46B, at the juncture of the tracer/buffer pump line 325 and the primary pump line 318 there is a portion of the diluent segment D which corresponds with and combines with the wash/diluent segment $W_1D_{W1}$ to form the intersample segment $W_1D_{W1}D$. Each of the tracer/buffer pump line 325 and primary pump line 318 include a following three second air segment $A_3$ which combines in the primary pump line. The tracer/buffer segment $T_1$ is positioned and sized to join with the sample/diluent segment $S_1D_{S1}$. The resultant flow from the mixing coil 325 is shown in FIG. 46C. Briefly, the resulting flow comprises a sample segment $S_1D_{S1}T_1$ followed consecutively by a three second air segment $A_3$, a wash/diluent segment $W_2D_{W2}D$, a three second air segment $A_3$, and a sample segment $S_2D_{S2}T_2$.

The antibody pump line 336 combines with the primary pump line 318 immediately upstream of the incubator 344. Antibody pump line 336 includes a diluent segment D which joins the wash/diluent segment $W_1D_{W1}D$, and a three second air segment follows thereafter. The antibody pump line 336 next includes an antibody or diluent segment $A/D_1$ which is sized and positioned to combine with the sample segment $S_1D_{S1}T_1$ in the primary pump line 318. As previously noted, the primary pump line 318 is useful for either a digoxin test or a T3U test. The T3U test does not involve the use of an antibody, and in such instance the antibody/diluent segment $A/D_1$ comprises simply a diluent segment. For the digoxin test, the segment $A/D_1$ comprises a digoxin antibody segment. Following the antibody/diluent segment $A/D_1$ is consecutively a three second air segment $A_3$, a diluent segment D, a three second air segment $A_3$, and an antibody/diluent segment $A/D_2$.

The resultant stream from combining the antibody pump line 336 and primary pump line 318, which is presented to the incubator and emerges therefrom, is shown in FIG. 46D. As indicated, the flow stream at this point in the primary pump line 318 comprises an alternating flow of sample and wash segments, the sample segment now including sample, diluent, tracer/buffer and antibody/diluent, and the wash segment now including wash and additional diluent. As shown in FIG. 46D, the flow stream at this point in the primary pump line 318 comprises, in consecutive order, a wash segment $W_1D_WD$, a three second air segment $A_3$, a sample segment $S_1D_{S1}T_1A/D_1$, a three second air segment $A_3$, a wash segment $W_2D_{W2}D$, a three second air segment $A_3$ and a sample segment $S_2D_{S2}T_2A/D_2$.

It has been shown that the pump lines associated with the primary pump line 318 include liquid and air segments which in particular respects are phased with one another to provide a sample segment having a combination of sample, diluent, tracer/buffer, and antibody or additional diluent. It will be appreciated that the phasing of these pump lines may be accomplished in various manners. A particular aspect of the present apparatus is the use of air segments to provide the phasing of these segmented flows. In prior art devices utilizing continuous flow of segmented streams, phasing has been provided by means of control of the various pump line lengths. However, these pump tubes are subject to considerable wear due to operation of the peristaltic or equivalent pump, and the phasing is subject to considerable change as a result. The present apparatus provides for self adjusting phasing of the flows such that the wear is not a significant factor. Of course, under any phasing technique there will be a point when the wear, distortion or ultimate failure of the tubes will prevent phasing to be maintained. In the present apparatus, the tolerances which will be permitted in performing the phasing operation may be predetermined such that when corrections have been made to a certain point, the need for replacement of tubing will be indicated. This and other aspects of the autophasing in the present apparatus will become apparent from the following discussion.

Preferably, the autophasing is based initially upon the movement of the transfer probe mechanism. Rather than controlling this movement, the flow on the other pump lines is modified to correspond with the flow in the sample pump line 316. In discussing the transfer probe mechanism, it was noted that several photodetectors are included which provide information to the microprocessor as to the location of the transfer probe at various times. The microprocessor therefore knows when a given three second air segment has been introduced into the sample pump line 316 at the transfer probe. Photodetector 416 is provided along sample pump line 316 downstream of the peristaltic pump, and detects when the given three second air bubble has progressed from the sample probe to that location. For the purposes of this discussion, the three second air segment immediately preceding the sample segment $S_1$ will be utilized.

The phasing of the segments in the various pump lines is accomplished initially by adjusting the lengths of the respective tubes connected at the downstream end of the peristaltic pump. Once this is accomplished, the appropriate relationships for the tubes is provided such that the relative times when the corresponding three second air segments are to arrive at each of the photodetectors is known, and automatic phasing thereafter can be accomplished. For example, the tubing lengths connected at the downstream end of the peristaltic pump for the sample pump line 316 and primary pump line 318 are adjusted so that the corresponding three second air segments will meet at the juncture of these two pump lines if they both have appeared at the photodetectors 416 and 419, respectively, at the same time. Under this arrangement, the phasing of the segments in the pump lines 316 and 318 may be accomplished by providing for the three second air segment to arrive at the photodetector 419 at the same time as the corresponding air segment arrives at the photodetector 416. The photodetector arrangement provides information to the microprocessor as to when a three second air segment has entered the sample pump line at the sample probe and has arrived at the photodetector 416, and also when a corresponding three second air segment has entered the primary pump line at valve 321, operated by the microprocessor, and has arrived at the photodetector 419. Thus, under appropriate microprocessor control, if a given three second air segment arrives at photodetector 419 before the arrival of the corresponding air segment at photodetector 416, then the closing of diluent valve 320 and opening of air valve 321 has occurred too soon and is delayed accordingly.

Similarly, photodetector 417 is provided along tracer/buffer pump line 325 (FIG. 46B) to provide phasing of that line with the primary pump line 318. As previously indicated, the portion of the pump line 325 connected at the downstream end of the peristaltic pump is initially adjusted to have a length to provide initial phasing between the lines 325 and 318. This may, for example, involve having the three second air segment arrive at the photodetector 417 at the same time as the corresponding air segment arrives at the photodetector 419. Alternatively, a predetermined time differential may be incorporated into the location of the corresponding air segments and their arrival at the respective photodetectors, with this time differential simply being programmed into the microprocessor. Thus, it may be desired to have a three second air segment arrive at the photodetector 417 five seconds after the corresponding air segment has arrived at the photodetector 419. In either event, the phasing for pump line 325 is accomplished in the same manner as previously indicated for the sample and primary pump lines. Thus, if an air segment $A_3$ arrives at photodetector 417 sooner or later than required for phasing with the corresponding air segment in primary pump line 318, then the timing of the tracer/buffer valves 329 or 330, and of the air valve 332, must be adjusted to account for the discrepancy. In like fashion, a photodetector 14 is provided along antibody/diluent pump line 336, and the phasing of corresponding air segments in the pump line 336 and primary pump line 318 is accomplished by control of the antibody valve 339 or diluent valve 331 and of the air valve 343.

After passing through the incubators, the fluids enter the discrete flow portion 20 of the analyzer. As before, two primary flow paths are utilized in the preferred RIA embodiment to accommodate the different tests to be conducted. The incubators are preferably sized such that the reactive process has substantially completed by the time the fluid segments have passed through the respective incubators. The sample segments, containing samples or standards to be measured, are analyzed in the discrete flow portion 20. The two primary flow paths are substantially identical, and only a first one of the paths will therefore be described in complete detail, with the other being described to note those differences which exist in the preferred embodiment.

The liquid and air segments leaving the T3U/digoxin incubator 344 move through line 362 and are delivered to collection cup 363. It is at the point of the collection cup that the analyzer transforms from the continuous flow mode to the discrete flow mode. The collection cup 363 preferably is constructed in accordance with the embodiment previously described with respect to FIGS. 34–36. The collection cup serves the purpose of collecting and retaining the sample segments which will subsequently be analyzed. In distinct contrast to certain prior art devices which operate on a continuous flow basis throughout, the present analyzer collects the sample fluid segments and periodically moves the segments to the analysis portion of the analyzer. In the typical prior art devices, the sample fluid segment is passed in the continuous fashion through, for example, a flow cell. The present analyzer, as will be further described below, collects a sample and retains it while the prior sample is being analyzed. The collected sample is then quickly passed through, for example, a resin column and then into the flow cell where it is retained for a period of time while the counting occurs.

In keeping with this purpose for the collection cup 363, it will be appreciated that alternative constructions from that shown in FIGS. 34–36 may suitably be used. For example, a type of debubbler could be used in which the desired sample segment is passed into a holding tube or cup where it is retained while the prior sample is being counted. The intermediate air and wash segments would then be removed to waste. However, the three second, phasing air bubbles would be lost and other provisions would have to be made for controlling the component operations in the discrete flow portion of the apparatus.

The collection cup 363 is connected by means of line 364 and associated valve 365 to a three way vlave 366. Valve 366 is used to direct the sample segments received through line 364 either to the T3U uptake column 367 or the digoxin column 368, depending upon the test being run. These columns are connected through a three way valve 369 to the T3U/digoxin flow cell 370 and through column waste line 371 and valve 372 to the waste retention bottle 290. Collection cup 363 is also connected through a waste line 373 and valve 374 to the waste retention bottle 290. In this manner, the vacuum pump 294 through its connection with the waste retention bottle 290 is operable to draw the liquid segments from collection cup 363 either directly to waste through waste line 373 or into the T3U uptake or digoxin columns and the flow cell 370.

In general, a sample segment to be analyzed is collected in the collection cup 363 until substantially all of the sample has been collected. The sample segment is then drawn under vacuum or by other discrete flow means through the appropriate column and then into the flow cell where it remains for a period of time during counting or other analysis. The wash segments in line 362 which have been provided between successive samples are then collected in the collection cup 363 and when the succeeding sample is presented to the collection cup the contents of the cup are evacuated to the waste retention bottle. This succeeding or second sample segment is then collected over a period of time in the collection cup. During the period of time when the wash segments are collected and evacuated and the second sample is collected, the first sample segment is counted in the flow cell and eventually evacuated to waste. Once this first sample segment is in the flow cell, the column which was used is washed and prepared for subsequent use.

To further clarify the operation of the chemistry section, a detailed description of the operation of the preferred embodiment as shown in FIG. 45 will now be presented. It is to be understood, however, that as previously indicated that the separation means and analysis means may vary as dictated by the tests being conducted. Preferably, each of the original sample segments is drawn into the analyzer for a period of sixty seconds, and a three second air segment is provided immediately preceding and immediately following each of the sample segments. As in the earlier portions of the analyzer, the three second air segments are preferably utilized to trigger certain of the operations, and the known time lengths of the sample segments are similarly utilized to control the analyzer operations. A photodetector 375 is provided at line 362 and detects the three second air segment preceding a sample segment to be analyzed. At this time, the collection cup waste valve 374 is opened for a period of two seconds to evacuate the waste fluid from the collection cup to the waste retention bottle. The time period is sufficiently long to similarly evacuate the remaining waste liquid in line 362 preceding the three-second air bubble. The waste valve 374 is then closed and the sample segment is collected in the cup 363.

Alternatively, the approximate time required for fluid to pass from the photodetector 375 to the collection cup 363 may be predetermined and programmed into the microprocessor. When this time has elapsed following the detection of the preceding three second air segment at photodetector 375, this indicates that this air segment has now reached the collection cup 363. At this time, valve 374 is opened for a period of two seconds to evacuate the waste fluid from the collection cup to the waste retention bottle. Valve 374 is then closed and the sample segment is collected in the cup 363.

The sample segment is permitted to collect in the collection cup 363 for a period of sixty seconds, the time length of the sample segment, and valves 365 and 376 are then opened to draw the first sample segment from the collection cup. At this time, air valve 377 and diluent valve 378 are closed and valves 366 and 369 are positioned to direct the first sample segment into either the T3U column 367 or the digoxin column 368. The waste valve 372 is also closed to assure that the first sample segment will be directed into the flow cell 370.

A photodetector 379 is provided on line 364 downstream of valve 365 to detect the presence of a three-second air segment immediately following the first sample segment. The arrival of the air segment, signifying the trailing end of the first sample segment, will occur prior to the arrival of the front end of the first sample segment at a photodetector 380, provided on line 381 leading from the T3U/digoxin flow cell to the waste bottle. When the three-second air segment following the first sample segment is detected at the photodetector 379, the diluent valve 378 is opened to provide a continuous liquid segment to the T3U uptake or digoxin column until the sample segment has arrived at the flow cell. Once the first sample segment is detected as having arrived at the photodetector 380, the diluent valve 378 and the flow cell waste valve 376 are closed and the analysis means, the gamma counter, is activated. At this time, the first sample segment has been passed through the appropriate T3U uptake or digoxin column and resides primarily in the flow cell, with the segment extending on both sides of the flow cell. This assures that the flow cell is fully occupied by the first sample segment and that only the first sample segment is contained in the flow cell while counting occurs.

It is perferable that the sample segments pass through the resin column in an upward flow through the resin. Surprisingly, it has been found that this reverse flow can be performed under the vacuum draw. As a result, the resin material does not pack down as with conventional, downward flow, and channeling is thereby minimized. A continual liquid flow passes through the column until the flow cell is filled with the sample segment, thus facilitating the upward or reverse flow in the resin column.

At the same time that the diluent valve 378 and flow cell waste valve 376 are closed, the column waste valve 372 and collection cup valve 365 are opened to evacuate the liquid, except for that in the flow cell, which is downstream of the collection cup 363. In particular, the valves are opened to evacuate any remaining portions of the first sample segment from the T3U uptake or digoxin column. The time required to evacuate first the first sample segment through the columns and into the flow cell and then the remaining liquids from the column through the waste valve 372 is sufficiently short that this is accomplished before the wash segments following the first sample segment are delivered to the collection cup 363.

The collection cup valve 365 is maintained open at this time for a period of two seconds, and is then closed and the diluent valve 378 is opened for a period of 10 seconds. The diluent valve 378 and the column waste valve 372 are closed simultaneously, thus causing the T3U or digoxin column, whichever was used for the first sample segment, to remain immersed in the diluent solution for a period of time while the first sample segment is being counted. This is advantageous since it further acts to cleanse the column and prevent carry over from one sample segment to a succeeding one.

After the gamma counter has been operating for a period of sixty seconds, the air valve 377 and flow cell waste valve 376 are opened for about 10 seconds, thus evacuating all fluid from the T3U uptake or digoxin column and from the flow cell. The column and flow cell are then rinsed by closing the air valve 377 and opening the diluent valve 378 for a short period of time, followed by closing the diluent valve 378 and reopening the air valve 377 to again clear the components of fluid. At this time, the three way valves 366 and 369 are positioned to direct the succeeding sample segment to the appropriate column.

While these various operations have been taking place with respect to the T3U or digoxin column and the T3U/digoxin flow cell, liquid wash and air segments have been presented to the collection cup 363. The collection cup waste valve 374 is normally in the closed position. As previously noted, after the first sample segment has been presented to the flow cell the collection cup valve 365 is opened for a period of two seconds to evacuate fluid from the line and the appropriate column. Valve 365 is then closed and the wash segments following the first sample segment are collected in the collection cup 363.

Disposal of these waste segments may be accomplished in various ways, but in the preferred embodiment the three second air segment following these wash segments and preceding the second sample segment is detected by the photodetector 375 and is utilized to activate the collection cup waste valve 374. When this three second air segment is detected at the photodetector 375, the collection cup waste valve 374 is opened for a period of two seconds, which is sufficient as previously noted with respect to the first sample segment, to evacuate the collected wash segments and the remaining wash segment portion in line 362 and preceding the air segment detected by the photodetector. The waste valve 374 is closed after the two second period and the second sample segment is collected for a period of sixty seconds.

Most preferably, the counting, rinsing and other operations performed with respect to the T3U and digoxin columns and flow cell are timed such that the three second air segment following the second sample segment is detected at the photodetector 375 after the rinse operation has been completed. At this time, the three way valves 366 and 369 have been appropriately positioned for the next test. Also at this time, air valve 377 and flow cell waste valve 376 are open and collection cup valve 365 and column waste valve 371 are closed. When the three second air segment trailing the second sample segment is presented to the photodetector 375, the air valve 377 is closed and the collection cup valve 364 is opened to evacuate the collected second sample segment through the appropriate column into the flow cell. In this manner, the operation of the discrete flow portion of the apparatus has been brought full cycle, and further proceeds in accordance with the earlier description respecting the first sample segment.

As previously noted, the discrete flow portion preferably comprises two primary flow paths which are substantially identical. The T4 incubator 345 connects through line 382 to a collection cup 383. Collection cup 383 connects through a collection cup line 384 and valve 385 to the T4 column 386. Collection cup 383 also connects through a line 387 and collection cup waste valve 388 to the waste bottle 290. Air line valve 389 and diluent valve 390 are similarly included to provide air or diluent to the column and flow cell. The T4 column 306 connects through line 391 to the T4 flow cell 392, which in turn connects through the flow cell waste line 393 and valve 394 to the waste bottle 290. The T4 column also connects directly through line 395 and associated valve 396 to the waste bottle.

In similar fashion to that described with respect to collection cup 363, the collection cup 383 and subsequent components operate to collect and test sample segments. A photodetector 408 is provided on line 382 to detect the three-second air segments immediately preceding and following the sample segments. As indicated with respect to photodetector 375, the photodetector 408 operates to trigger the subsequent valving to deliver the sample segments to the T4 column 386 and flow cell 392, and the waste segments through line 387 to the waste retention bottle 290. Similarly, photodetectors 409 and 410 are provided and operate in the manner of photodetectors 379 and 380, respectively.

A cleaning solution is provided in container 411, which is suitably maintained in the refrigerator unit 24. The cleaning solution container 411 is connected through line 412 and associated valve 413 to the main diluent line 414. The cleaning solution is provided to clean many of the system components before and/or after test runs. During a cleaning operation, the main diluent valve 414 on diluent line 314 is closed and the cleaning solution valve 413 is opened to provide cleaning solution to the apparatus through the diluent lines. After sufficient time has elapsed to perform the cleaning operation, the cleaning solution valve 413 is closed and the main diluent valve 415 is opened to provide diluent to the system and components. Preferably, the diluent is fed through the system for a period of time sufficient to substantially eliminate traces of the cleaning solution, and at this time the system is suitable for test runs.

The present apparatus perferably includes a calculator for receiving the raw data and counts and for processing the data to determine the desired sample information. A suitable calculator is, for example, the Rockwell International AIM 65. In addition, a component such as a Hewlett Packard 9815 may be interfaced with the calculator to plot graphs of the test results. The data for standards is curve fit and the unknown test samples are compared with the standard curves. The printer/calculator is also preferably employed to monitor the apparatus components and to indicate operating conditions and error or alert conditions.

What is claimed is:

1. An automated chemical testing apparatus which comprises:

continuous flow means for providing a continuous flow stream of alternating sample and intersample fluid segments, each intersample fluid segment including a liquid wash segment;

collecting means for separately collecting each of the sample segments and for collecting the intersample segments including the wash segments separately of the sample segments;

analysis means for analyzing the sample segments;

waste collection means for collecting waste fluids said analysis means and said waste collection means each being connected with said collecting means; and discrete flow means for alternately flowing a collected sample segment to said analysis means and an intersample segment to said waste collection means.

2. The apparatus of claim 1 in which said discrete flow means is for flowing the collected sample segments to said analysis means at a volumetric flow rate higher than the volumetric flow rate of the continuous flow stream.

3. The apparatus of claim 1 in which each of the sample segments is maintained stationary while the analysis means is analyzing the sample segment.

4. The apparatus of claim 2 in which each of the sample segments is maintained stationary while the analysis means is analyzing the sample segment.

5. The apparatus of claim 1 in which said discrete flow means includes a vacuum means for drawing the collected sample segments under vacuum into said analysis means.

6. The apparatus of claim 2 in which said discrete flow means includes a vacuum means for drawing the collected sample segments under vacuum into said analysis means.

7. The apparatus of claim 1 in which said continuous flow means provides intersample segments including a plurality of liquid wash segments separated by interwash air segments, and further provides a leading air segment adjacent the preceding sample segment and a following air segment adjacent the following sample segment.

8. The apparatus of claim 1 in which said collecting means comprises a receptacle connected to each of said analysis means and said waste collection means, said continuous flow means further being for delivering the continuous flow stream of alternating sample and intersample segments into the receptacle, said collecting means further comprising control means for directing the sample segments into said analysis means and for directing the intersample segments into the waste collection means.

9. The apparatus of claim 8 in which said continuous flow means provides intersample segments including a plurality of liquid wash segments separated by interwash air segments, and further provides a leading air segment adjacent the preceding sample segment and a following air segment adjacent the following sample segment.

10. The apparatus of claim 9 in which the leading and following air segments are each at least twice as large as any of the interwash air segments, said control means including bubble detecting means for detecting the leading and following air segments, said control means further being for directing the sample segments into said analysis means and for directing the intersample segments into the waste collection means in response to the detection of the leading and following air segments by the bubble detecting means.

11. The apparatus of claim 1 in which said continuous flow means includes flow path means for containing and transporting sample and intersample segments to said collecting means, sampling means for drawing sample and intersample segments into said flow path means, pump means for moving the sample and intersample segments through the flow path means, and reagent means for introducing reagent into the sample segments intermediate the sampling means and the collecting means.

12. The apparatus of claim 11 in which said flow path means includes an incubator through which the sample and intersample segments are transported intermediate of the sampling means and the collecting means.

13. The apparatus of claim 12 and further including diluent means for introducing diluent into the sample segments intermediate the sampling means and the collecting means.

14. The apparatus of claim 1 in which the sample segments as collected by said collecting means includes test components and waste components, said analysis means including a separator means for separating the test components from the waste components, said analysis means further including a measuring means for measuring an attribute of the test components of the sample segments, said discrete flow means further being for flowing the test components to the measuring means and for flowing the waste components to said waste collection means.

15. The apparatus of claim 14 in which said continuous flow means includes flow path means for containing and transporting sample and intersample segments to said collecting means, sampling means for drawing sample and intersample segments into said flow path means, pump means for moving the sample and intersample segments through the flow path means, and reagent means for introducing reagent into the sample segments intermediate the sampling means and the collecting means.

16. The apparatus of claim 15 in which said flow path means includes an incubator through which the sample and intersample segments are transported intermediate of the sampling means and the collecting means.

17. The apparatus of claim 16 and further including diluent means for introducing diluent into the sample segments intermediate the sampling means and the collecting means.

* * * * *